(12) United States Patent
Kozikowski et al.

(10) Patent No.: US 6,479,470 B1
(45) Date of Patent: Nov. 12, 2002

(54) LIGANDS FOR METABOTROPIC GLUTAMATE RECEPTORS AND INHIBITORS OF NAALADASE

(75) Inventors: Alan P. Kozikowski, Princeton, NJ (US); Jarda T. Wroblewski, Kensington, MD (US); Fajun Nan, Washington, DC (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 09/559,978

(22) Filed: Apr. 27, 2000

Related U.S. Application Data

(60) Provisional application No. 60/188,031, filed on Mar. 9, 2000, provisional application No. 60/166,915, filed on Nov. 22, 1999, and provisional application No. 60/131,627, filed on Apr. 28, 1999.

(51) Int. Cl.[7] .................. A61K 31/66; A61K 31/19; C07F 9/28
(52) U.S. Cl. ................. 514/75; 514/574; 562/8; 562/10; 562/24
(58) Field of Search ............... 514/75, 574; 562/8, 562/10, 24

(56) References Cited

U.S. PATENT DOCUMENTS

| | | | |
|---|---|---|---|
| 3,527,789 A | 9/1970 | Payne | 260/485 |
| 5,672,592 A | 9/1997 | Jackson et al. | 514/75 |
| 5,795,877 A | 8/1998 | Jackson et al. | 514/75 |
| 5,824,662 A | 10/1998 | Slusher et al. | 514/75 |
| 5,880,112 A | 3/1999 | Jackson et al. | 514/121 |
| 6,071,965 A * | 6/2000 | Jackson et al. | 514/574 |

FOREIGN PATENT DOCUMENTS

| | | |
|---|---|---|
| EP | 0 878 463 A1 | 11/1998 |
| WO | WO 97/48399 | 12/1997 |
| WO | WO 97/48400 | 12/1997 |
| WO | WO 97/48409 | 12/1997 |
| WO | WO 98/13046 | 4/1998 |
| WO | WO 98/45256 | 10/1998 |
| WO | WO 98/45257 | 10/1998 |
| WO | WO 99/33847 | 7/1999 |
| WO | WO 00/64911 | 11/2000 |
| WO | WO 01/01974 A2 | 1/2001 |

OTHER PUBLICATIONS

Jackson et al.;"Design, Synthesis, and Biological Activity of a Potent Inhibitor of the Neuropeptidase N–Acetylated α–Linked Acidic Dipeptidase", J. Med. Chem. 39: 619–622 (1996).

Nan F. et al.; "Dual Function Glutamate–Related Ligands: Discovery of a Novel, Potent Inhibitor of Glutamate Carboxypeptidase II Possessing mGluR3 Agonist Activity", J. Med. Chem. 43: 772–774 (2000).

Carter et al.; "Prostate–Specific Membrane Antigen is a Hydrolase with Substrate and Pharmacologic Characteristics of a Neuropeptidase", Proc. Natl. Acad. Sci. USA 93: 749–753 (Jan. 1996).

Slusher et al.; "RAT Brain N–Acetylated α–Linked Acidic Dipeptidase Activity", The Journal of Biological Chemistry 265 (34): 21297–21301 (1990).

Slusher et al.; "Immunocytochemical Localization of the N–Acetyl–Aspartyl–Glutamate (NAAG) Hydrolyzing Enzyme N–Acetylated α–Linked Acidic Dipeptidase (NAALADase)", The Journal of Comparative Neurology 315: 217–229 (1992).

Kozikowski et al.; "Design of Remarkably Simple, Yet Potent Urea–Based Inhibitors of Glutamate Carboxypeptidase II (NAALADase)", J. Med. Chem. 44(3): 298–301, (2001).

Izdebski and Pawlak, "Synthesis of N,N'—Carbonyl–bis amino Acids and N,N'–Carbonyl–bis–peptides", Polish J. Chem. 71: 1066–1074, (1997).

6001 Chemical Abstracts, Columbus, Ohio, US; vol. 101(27), XP 002196919, (Oct. 22, 1984).

International Search Report Completed on Apr. 23, 2002 and mailed on May 5, 2002.

* cited by examiner

Primary Examiner—Mukund J. Shah
Assistant Examiner—Tamthom N. Truong
(74) Attorney, Agent, or Firm—Dana M. Gordon; Foley Hoag LLP

(57) ABSTRACT

The present invention relates to novel compounds and formulations thereof which compounds are ligands, e.g., agonists or antagonists, for a metabotropic glutamate receptor or a NAALADase enzyme or both. The present invention also relates to methods of modulating the activity of a metabotropic glutamate receptor or a NAALADase enzyme or both, e.g., in a subject in need thereof, using a compound or formulation of the present invention. The present invention also relates to methods of treating a subject suffering from a chronic or acute disease, malady or condition due at least in part to an abnormality in the activity of an endogenous metabotropic glutamate receptor or a NAALADase enzyme or both, using a compound or formulation of the present invention.

67 Claims, 15 Drawing Sheets

| Compound | Activity Against NAAG Peptidase | Activity Against Metabotropic Glutamate Receptors |
|---|---|---|
| 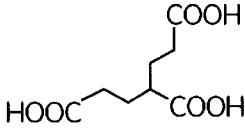 | 23% INHIBITION AT 100 μM | partial agonist of mGluR3 |
| 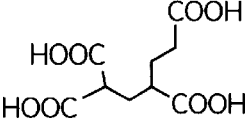 | 44% INHIBITION AT 100 μM | partial agonist of mGluR3 |
| 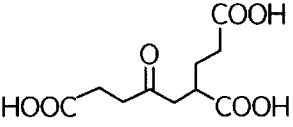 | 35% INHIBITION AT 100 μM | partial agonist of mGluR3 |
| 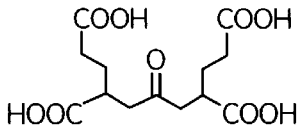 | 64% INHIBITION AT 100 μM | EC50 > 300 μM |
| 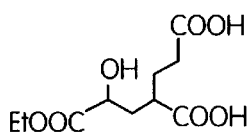 | 23% INHIBITION AT 100 μM | partial agonist of mGluR3 |
| 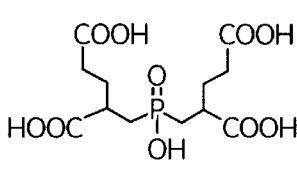 | IC50 = 21.7 ± 2.1 nM | EC50 ≅ 30 μM |
| 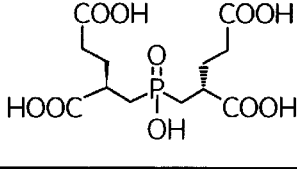 | IC50 = 84.0 ± 20.8 nM | |
| 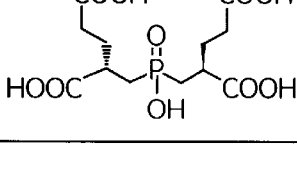 | IC50 = 6.9 ± 0.7 nM | |
Fig. 10

| Compound | Activity Against NAAG Peptidase | Activity Against Metabotropic Glutamate Receptors |
|---|---|---|
| [structure: phosphinate diacid] | IC50 = 22.3 ± 5.8 nM | |
| [structure: hydroxy diacid] | 20% INHIBITION AT 1 μM | partial agonist of mGluR3 |
| [structure: amino diacid] | 4% INHIBITION AT 1 μM | partial agonist of mGluR2 and mGluR3 |
| [structure: oxamide diacid] | 9% INHIBITION AT 1 μM | partial agonist of mGluR2 and mGluR3 |
| [structure: urea diacid] | IC50 = 47 nM | partial agonist of mGluR2 and mGluR3 |
| [structure: OAc diacid] | 13% INHIBITION AT 1 μM | |
| [structure: urea diacid stereoisomer] | 67% INHIBITION AT 100 μM | |

Fig. 11

| Compound | Activity Against NAAG Peptidase | Activity Against Metabotropic Glutamate Receptors |
|---|---|---|
| MeOOC-CH(COOMe)-NH-C(=O)-NH-CH(COOMe)-COOMe | 3% INHIBITION AT 100 μM | |
| HOOC-CH(COOH)-NH-C(=O)-NH-CH(COOH)-COOH | 97% INHIBITION AT 100 μM | |
| MeOOC-CH(COOMe)-NH-C(=S)-NH-CH(COOMe)-COOMe | 70% INHIBITION AT 100 μM | |
| HOOC-CH(COOH)-NH-C(=NH)-NH-CH(COOH)-COOH | 57% INHIBITION AT 100 μM | |
| HOOC-CH(CH2COOH)-NH-C(=O)-NH-CH(CH2COOH)-COOH | IC50 = 3800 ± 600 nM | |
| HOOC-CH(CH2COOH)-NH-C(=O)-NH-CH(CH2CH2COOH)-COOH | IC50 = 46.1 ± 1.4 nM | |

Fig. 12

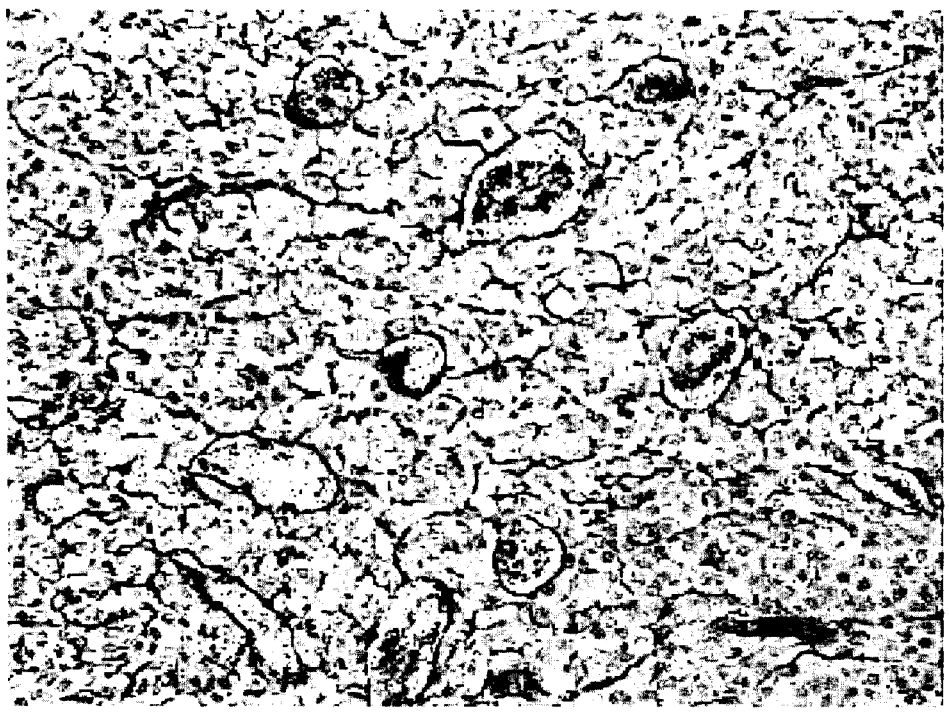
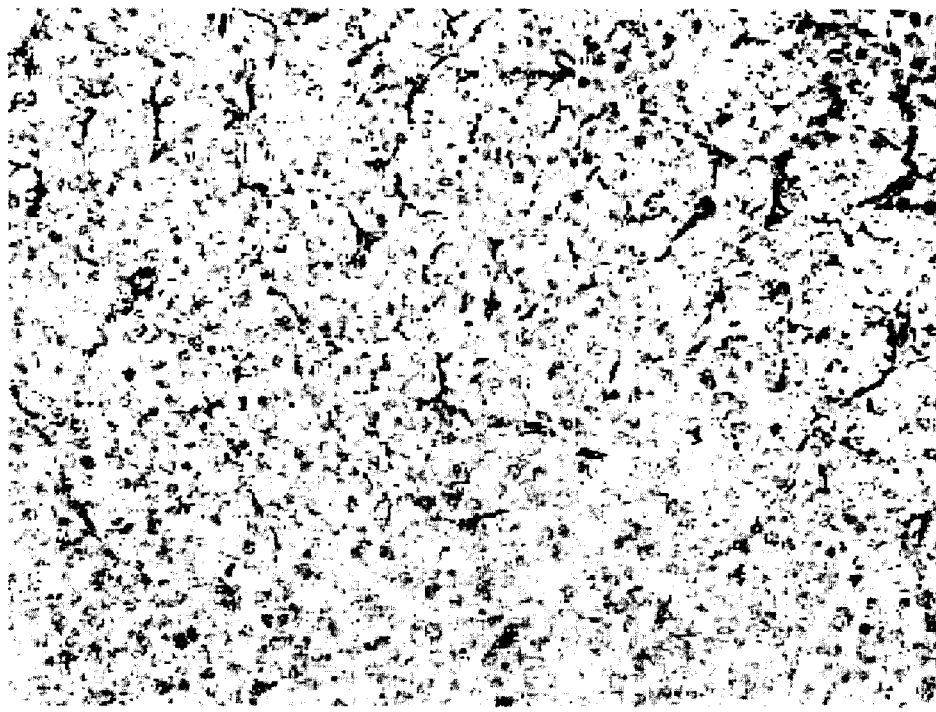
Fig. 13

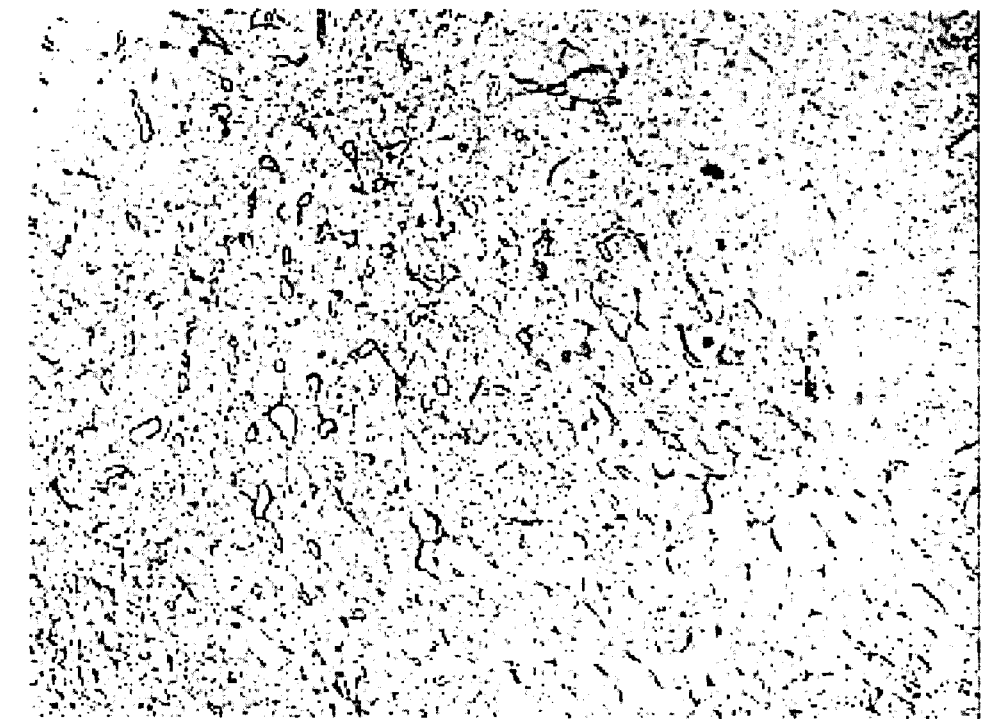
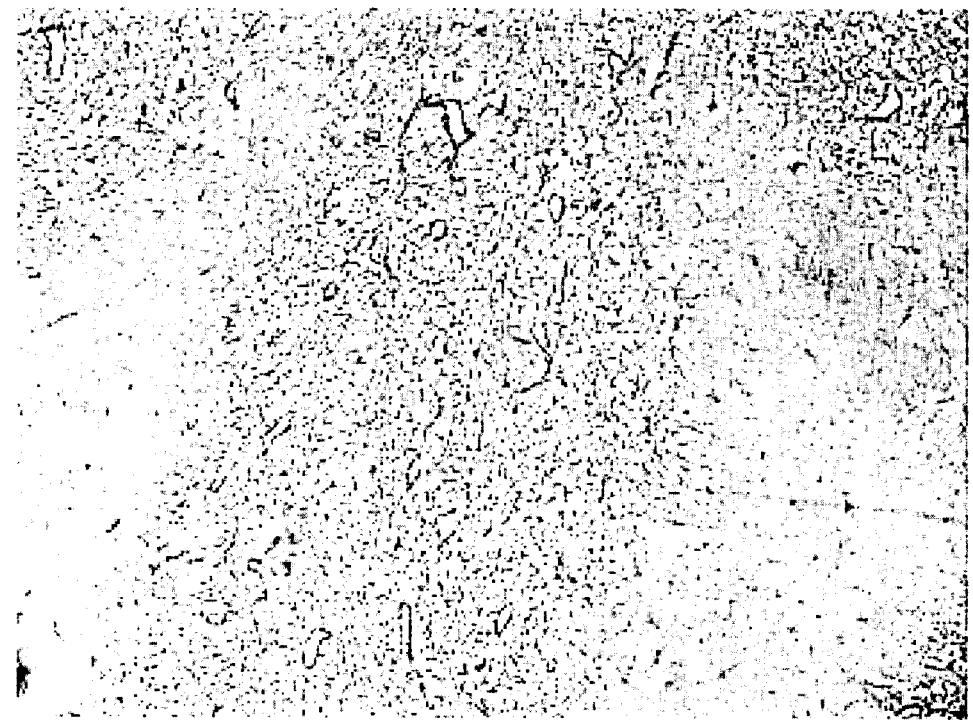
Fig. 14

LIGANDS FOR METABOTROPIC GLUTAMATE RECEPTORS AND INHIBITORS OF NAALADASE

RELATED APPLICATIONS

This application claims the benefit of priority to: U.S. Provisional Patent Application Ser. No. 60/188,031, filed Mar. 9, 2000; U.S. Provisional Patent Application Ser. No. 60/166,915, filed Nov. 22, 1999; and U.S. Provisional Patent Application Ser. No. 60/131,627, filed Apr. 28, 1999.

BACKGROUND OF THE INVENTION

Glutamate is a major excitatory neurotransmitter in the mammalian central nervous system. The neurotransmitter activity of glutamate is primarily mediated by ligand-gated ion channels. The observation that glutamate also induces responses mediated by second messengers has led to the discovery of a distinct group of glutamate receptors coupled to G proteins, termed metabotropic receptors (mGluRs). Schoepp and Conn, Trends Pharmacol. Sci. 14: 13–20 (1993). The first described action of the glutamate metabotropic receptors was inositol phospholipid (PI) hydrolysis. Nicoletti et al., J. Neurochem. 46: 40–46 (1986) and Sugiyama et al., Nature 325: 531–533 (1987). Molecular cloning techniques have revealed a large family of metabotropic receptors with distinct transduction mechanisms, patterns of expression and sensitivities to glutamate agonists. Schoepp and Conn, supra.

Consistent with the molecular heterogeneity observed for the metabotropic receptors, electrophysiological studies have suggested diverse roles for these receptors in synaptic plasticity, presynaptic inhibition and regulation of cell excitability by ion channel modulation. Bashir et al., Nature 363: 347–363 (1993); Linden et al., Neuron 7: 81–89 (1991); Baskys and Malenka, J. Physiol. (Lond.) 444: 687–701 (1991); Charpak et al. Nature 347: 765–767 (1990); and Lester and Jahr, Neuron 5: 741–749 (1990). However, the specific mGluR receptors mediating these cellular functions are largely undefined.

Evidence for a physiological role for specific mGluR subtypes has been derived from work with selective agonists and antagonists of the receptors. For example, (1S,3R)-1-aminocyclopentane-1,3-dicarboxylic acid (ACPD) is a selective and potent activator of the mGluR1, mGluR2, mGluR3 and mGluR5 receptors. Masu et al., Nature 349: 760–765 (1991); Abe et al., J. Biol. Chem. 267: 13361–13368 (1992); Tanabe et al., Neuron 8: 169–179 (1992); and Tanabe et al., J. Neurosci. 13: 1372–1378 (1993). L-2-amino-4-phosphonobutryic acid (L-AP4) has been shown to activate mGluR4 and mGluR6. Id., Thomsen et al., Eur. J. Pharmacol. 227: 361–362 (1992); Nakajima et al., J. Biol. Chem. 268:11868–11873 (1993). L-AP4 inhibits transmitter release and voltage-dependent calcium entry in selected brain and spinal cord neurons. Koerner and Cotman, Brain Res. 216: 192–198 (1981); Trombley and Westbrook, J. Neurosci. 12:2–43–2050 (1992); and Sahara and Westbrook, J. Neurosci. 13: 3041–3050 (1993). But in retinal bipolar neurons, postsynaptic L-AP4 receptors activate aphosphodiesterase. Nawy and Jahr, Nature 346: 269–271 (1990).

Multiple mGluR subtypes can be present within the same group of neurons. As the cellular and subcellular localization of specific mGluRs may be important in shaping incoming sensory information, it is important to identify other receptors of the mGluR group. Once identified, specific agonists and antagonists can be prepared to modulate the responses associated with the receptor. Quite surprisingly, the present invention identifies a L-AP4 sensitive receptor that modulates transmitter release in neurons that express neither mGluR4 nor mGluR6, and fulfills other related needs.

As alluded to above, the metabotropic glutamate receptors (mCluRs) are a heterogeneous family of G-protein linked receptors that are coupled to multiple second messenger systems. These include the negative modulation of adenylate cyclase, activation of phosphoinositide-specific phospholipase C, and modulation of ion channel currents [Science, 1992, 258, 597; Trends in Pharmacol. Sci.1993, 14, 13; J.Med.Chem. 1995, 1417]. Three types of mGluR receptors have been identified. The group I receptors couple to phosphoinositide hydrolysis and include $mGluR_1$ and $mGluR_5$; group II receptors are coupled to the inhibition of cyclic adenosine 5'-monophosphate(cAMP) formation and include $mGluR_2$ and $mGluR_3$. Group III receptors ($mGluR_4$, $mGluR_6$, $mGluR_7$ and $mGluR_8$) also couple negatively to cAMP. Each of the mGluR subtypes is thus distinguished on the basis of its pharmacology and sequence homology. Excessive activation of glutamate receptors or disturbances in the cellular mechanisms that protect against the potential adverse consequences of physiological glutamate receptor activation have been implicated in the pathogenesis of a diverse number of neurological disorders. These disorders include epilepsy, ischaemia, central nervous system trauma, neuropathic pain, and chronic neurodegenerative diseases. Because of the ubiquitous distribution of glutamatergic synapses, mGluRs have the potential to participate in a wide variety of functions in the CNS. In addition, because of the wide diversity and heterogeneous distribution of the mGluRs subtypes, the opportunity exists for developing highly selective drugs that affect a limited number of CNS functions. The mGluRs therefore provide novel targets for the development of therapeutic agents that could have a dramatic impact on treatment of a wide variety of psychiatric and neurological disorders.

Ischemia, a localized tissue anemia resulting from the obstruction of the inflow of arterial blood, can cause extensive damage when it occurs in the brain or central nervous system. Central nervous tissue, and to a lesser extent peripheral nervous tissue, has poor reparative abilities. Thus damage to nervous tissue causes significant permanent disability and is a frequent cause of death. Damage to nervous tissue may occur in many ways, not only through ischemia in cerebrovascular accidents, but also in cerebral circulatory disturbances, episodes of absolute and relative hypoxia, from metabolic disturbances and from various forms of trauma.

Global ischemia occurs under conditions in which blood flow to the entire brain ceases for a period of time, such as may result from cardiac arrest. Focal ischemia occurs under conditions in which a portion of the brain is deprived of its normal blood supply, such as may result from thromboembolytic occlusion of a cerebral vessel, traumatic head injury, edema, and brain tumors. In areas of focal ischemia or damage, there is a core of more profound damage, surrounded by a perifocal penumbra of lesser damage. This is because the neurons in thepenumbra can for a time maintain homeostasis thus rendering them potentially more salvageable by pharmacological agents.

Both global and focal ischemic conditions have the potential for producing widespread neuronal damage, even if the ischemic condition is transient. Although some permanent neuronal injury may occur in the initial mixture following cessation of blood flow to the brain, the damage in global and focal ischemia occurs over hours or even days following the ischemic onset. Much of this neuronal damage is attributed to glutamate toxicity and secondary consequences of reperfusion of the tissue, such as the release of vasoactive products by damaged endothelium, and the release by the damaged tissues of cytotoxic products including free radicals, leukotrienes, and the like.

Glutamate neurotoxicity, which is a major factor in ischemic neuronal injury, appears to begin with resumption of oxidative metabolism and thus occurs both during reversible ischemia and during recovery. Many attempts have been made to avoid this problem by blocking of the various receptors including NMDA receptors, AMPA receptors, Kainate receptors, and MGR receptors, which are stimulated by glutamate and are also strongly involved in nerve cell death occurring after the onset of global or focal ischemia. When ischemia occurs, such as during a stroke or heart attack, there is an excessive release of endogenous glutamate, resulting in the overstimulation of NMDA receptors, AMPA receptors, Kainate receptors, and MGR receptors. Interaction of the glutamate with these receptors causes the ion channel associated with these receptors to open, allowing a flow of cations across the cell membrane. This flux of ions, particularly $Ca^{2+}$ into the cells, plays an important role in nerve cell death.

Prostate cancer is now the leading form of cancer among men and the second most frequent cause of death from cancer in men. It is estimated that more than 165,000 new cases of prostate cancer were diagnosed in 1993, and more than 35,000 men died from prostate cancer in that year. Additionally, the incidence of prostate cancer has increased by 50% since 1981, and mortality from this disease has continued to increase. Previously, most men died of other illnesses or diseases before dying from their prostate cancer. We now face increasing morbidity from prostate cancer as men live longer and the disease has the opportunity to progress. Current therapies for prostate cancer focus exclusively upon reducing levels of dihydrotestosterone to decrease or prevent growth of prostate cancer. In addition to the use of digital rectal examination and transrectal ultrasonography, prostate-specific antigen (PSA) concentration is frequently used in the diagnosis of prostate cancer, PSA is a protein produced by prostate cells and is frequently present at elevated levels in the blood of men who have prostate cancer. PSA has been shown to correlate with tumor burden, serve as an indicator of metastatic involvement, and provide a parameter for following the response to surgery, irradiation, and androgen replacement therapy in prostate cancer patients. It should be noted that Prostate Specific Antigen (PSA) is a completely different protein from Prostate Specific Membrane Antigen (PSMA). The two proteins have different structures and functions and should not be confirmed because of their similar nomenclature.

In 1993, the molecular cloning of a prostate-specific membrane antigen (PSMA) was reported as a potential prostate carcinoma marker and hypothesized to serve as a target for imaging and cytotoxic treatment modalities for prostate cancer. Antibodies against PSMA have been described and examined clinically for diagnosis and treatment of prostate cancer. In particular, Indium-111 labelled PSMA antibodies have been described and examined for diagnosis of prostate cancer and itrium-labelled PSMA antibodies have been described and examined for the treatment of prostate cancer.

PSMA is expressed in prostatic ductal epithelium and is present in seminal plasma, prostatic fluid and urine In 1996, it was found that the expression of PSMA cDNA actually confers the activity of NAALADase. This is entirely unexpected because until recently NAALADase research has been limited to its role in the brain and its effect on neurotransmitters whereas PSMA has been described and examined for the diagnosis and therapy of prostate cancer.

The dipeptide NAAG is an abundant nervous system specific peptide which is present in synaptic vesicles and released upon neuronal stimulation in several systems. As a major peptidic component of the brain, NAAG is present in levels comparable to that of the major inhibitory neurotransmitter gamma-aminobutyric acid (GADA). Although NAAG was first isolated in 1964, there was little activity toward elucidating its role in the CNS until the deleterious nature of excess glutamate in a variety of disease states became apparent. Due to its structural similarity to glutamate, NAAG has been suggested to have a variety of roles similar to those of glutamate itself, including functioning as a neurotransmitter or a cotransmitter, neuromodulator, or as a precursor of the neurotransmitter glutamate. NAAG has elicited excitatory responses both in vitro ad in vivo, but is significantly less potent than glutamate.

In 1988, a brain enzyme, NAALADase, was identified which hydrolyzes NAAG to N-acetylaspartate (NAA) and glutamate. NAALADase, which derives its name from its structural specificity for N-acctylated acidic dipeptides, is a membrane-bound metallopeptidase having a denatured molecular mass of 94 kDa[x], that catabolizes NAAG to N-acetylaspartate (NAA) and glutamate. It has been demonstrated that [$^3$H]NAAG is degraded in vivo by an enzyme with the pharmacological characteristics of NAALADase, which supports a role for NAALADase in the metabolism of endogenous NAAG.

Rat NAALADase activity has been extensively characterized and demonstrates a high affinity for hydrolysis of its putative substrate NAAG, with a Km=140 nM. Recently, NAALADase also has been shown to cleave the non-acetylated peptide, aspartylglutamate, with high affinity. Research has also found that the enzyme is membrane-bound, stimulated by chloride ions, and inhibited by polyvalent cation chelators, suggesting that it is a metallopeptidase.

In animals, NAALADase is enriched in synaptic plasma membranes and is primarily localized to neural tissue and the kidneys. NAALADase has not been found in large quantities in the mammalian liver, heart, pancreas, or spleen. Examination of NAAG and NAALADase has been conducted for several different human and animal pathological conditions. It has been demonstrated that intra-hippocampal injections of NAAG elicit prolonged seizure activity. More recently, it was reported that rats genetically prone to epileptic seizures have a persistent increase in their basal level of NAALADase activity. These observations are consistent with the hypothesis that increased availability of synaptic glutamate elevates seizure susceptibility, and suggest that NAALADase inhibitors may provide anti-epileptic activity.

NAAG and NAALADase have also been implicated in the pathogenesis of ALS and in the pathologically similar animal disease called Hereditary Canine Spinal Muscular Atrophy (HCSMA). It has been shown that concentrations of NAAG and its metabolites-NAA, glutamate and aspartate-are elevated two- to three-fold in the cerebrospinal fluid of ALS patients and HCSMA dogs.

In addition, NAALADase activity is significantly increased (two- to three-fold) in post-mortem spinal cord tissue from ALS patients and HCSMA dogs. Although highly speculative, NAALADase inhibitors may be clinically useful in curbing the progression of ALS if increased metabolism of NAAG is responsible for the alterations of CSF levels of these acidic amino acids and peptides. Abnormalities in NAAG levels and NAALADase activity have also been documented in post-mortem schizophrenic brain, specifically in the prefrontal and limbicbrain regions, underscoring the importance of examining the metabolism of NAAG in the pathophysiology of schizophrenia. The identification and purification of NAALADase led to the proposal of another role for NAAG: specifically that the dipeptide may serve as a storage form of synaptic glutamate.

Only a few NAALADase inhibitors have been identified and those that have been identified have only been used in non-clinical neurological research. Examples of such inhibitors include general metallopeptidase inhibitors such as o-phenanthrolene, metal chelators such as EGTA and EDTA, and peptide analogs such as quisqualic acid and beta-NAAG.

SUMMARY OF THE INVENTION

Certain embodiments of the present invention relate to new ligands for metabotropic glutamate receptors and compositions comprising the ligands. The pharmaceutical compositions may be used to influence glutamate receptor-controlled cells, including neurons and glial cells in the central nervous system.

In additional embodiments, the present invention consists of inhibitors of NAALADase enzyme activity and compositions comprising them. Additional embodiments of the present invention consist of methods of treatment of glutamate abnormalities and associated nervous tissue insult in a animal by inhibition of NAALADase enzyme with the aforementioned inhibitors or compositions thereof.

BRIEF DESCRIPTION OF THE FIGURES

FIG. 10 depicts certain compounds of the present invention, their activity against NAAG peptidase, and their activity against certain metabotropic glutamate receptors.

FIG. 11 depicts certain compounds of the present invention, their activity against NAAG peptidase, and their activity against certain metabotropic glutamate receptors.

FIG. 12 depicts certain compounds of the present invention, their activity against NAAG peptidase, and their activity against certain metabotropic glutamate receptors.

FIG. 13 depicts at low magnification the antiangiogenic effects of a compound of the present invention on a glioblastoma xenograft.

FIG. 14 depicts at high magnification the antiangiogenic effects of a compound of the present invention on a glioblastoma xenograft.

FIG. 16 presents the neuroprotective action of ABHxD-I, 2-aminobicyclo[2.1.1]hexane-2,5-dicarboxylic acid, in three models of NMDA toxicity which shows a lack of effect in cultures of pure neurons without glia (A), while significant protection is seen in the model using mixed cortical neuronal-glia cultures (B) and when neurons are rescued with medium from glial cells exposed to the protective compound (C). Control refers to cells treated only with NMDA (without the protective compound) ABHxD was used at 10 $\mu$M concentration. Bars represent means and SEM from 16–30 measurements.

FIG. 17 shows the effects of FN compounds at 300 $\mu$M on NMDA toxicity in mixed cultures of cortical neuronal-glial cells (model B). Control refers to cells treated only with NMDA (without the protective compound). ABHxD-1 (10 $\mu$M) was used as a positive control. Bars represent means and SEM from 8–40 measurements.

FIG. 18 shows the effects of FN6 enantiomers at 100 $\mu$M on NMDA toxicity in mixed cultures of cortical neuronal-glial cells (model B). Control refers to cells treated only with NMDA (without the protective compound). ABHxD-1 (10 $\mu$M) was used as a positive control. Bars represent means and SEM from 8–11 measurements.

FIG. 19 shows the effects of FN6 enantiomers at 100 $\mu$M on NMDA toxicity in cortical neuronal cells exposed to medium from drug-treated glial cells (model C). Control refers to cells treated only with NMDA (and medium from untreated glia). ABHxD-1 (10 $\mu$M) was used as a positive control. Results with the Guilford compound PMPA are shown for comparison. Bars represent means and SEM from 12–30 measurements.

FIG. 20 shows the effects of FN compounds at 100 $\mu$M on NMDA toxicity in cortical neuronal cells exposed to medium from drug-treated glial cells (model C). Control refers to cells treated only with NMDA (and medium from untreated glia). ABHxD-1 (10 $\mu$M) was used as a positive control. Bars represent means and SEM from 8–61 measurements.

DETAILED DESCRIPTION OF THE INVENTION

Figure 1:
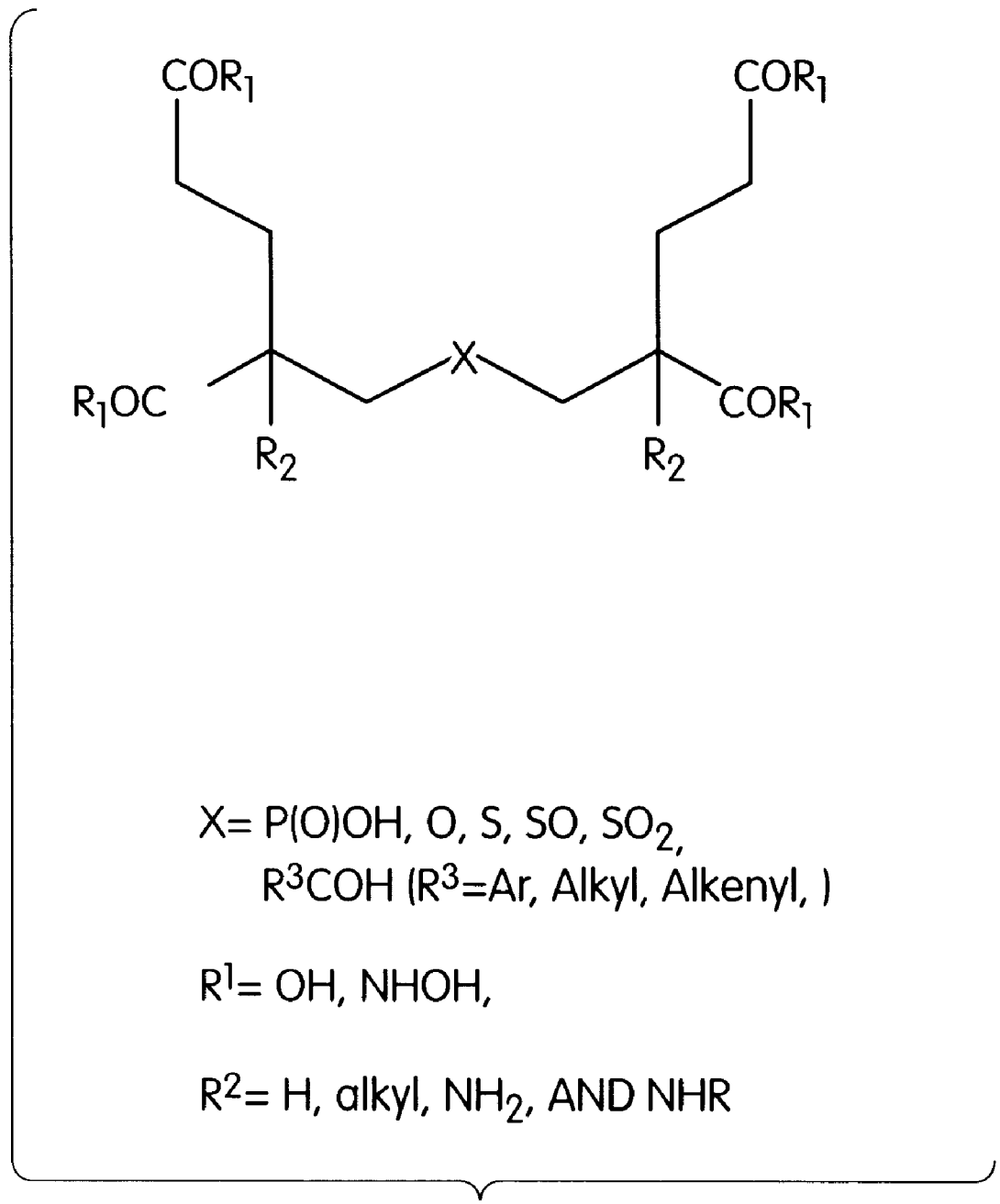
FIG. 1 depicts certain preferred embodiments of the compounds of the present invention.
Figure 2:
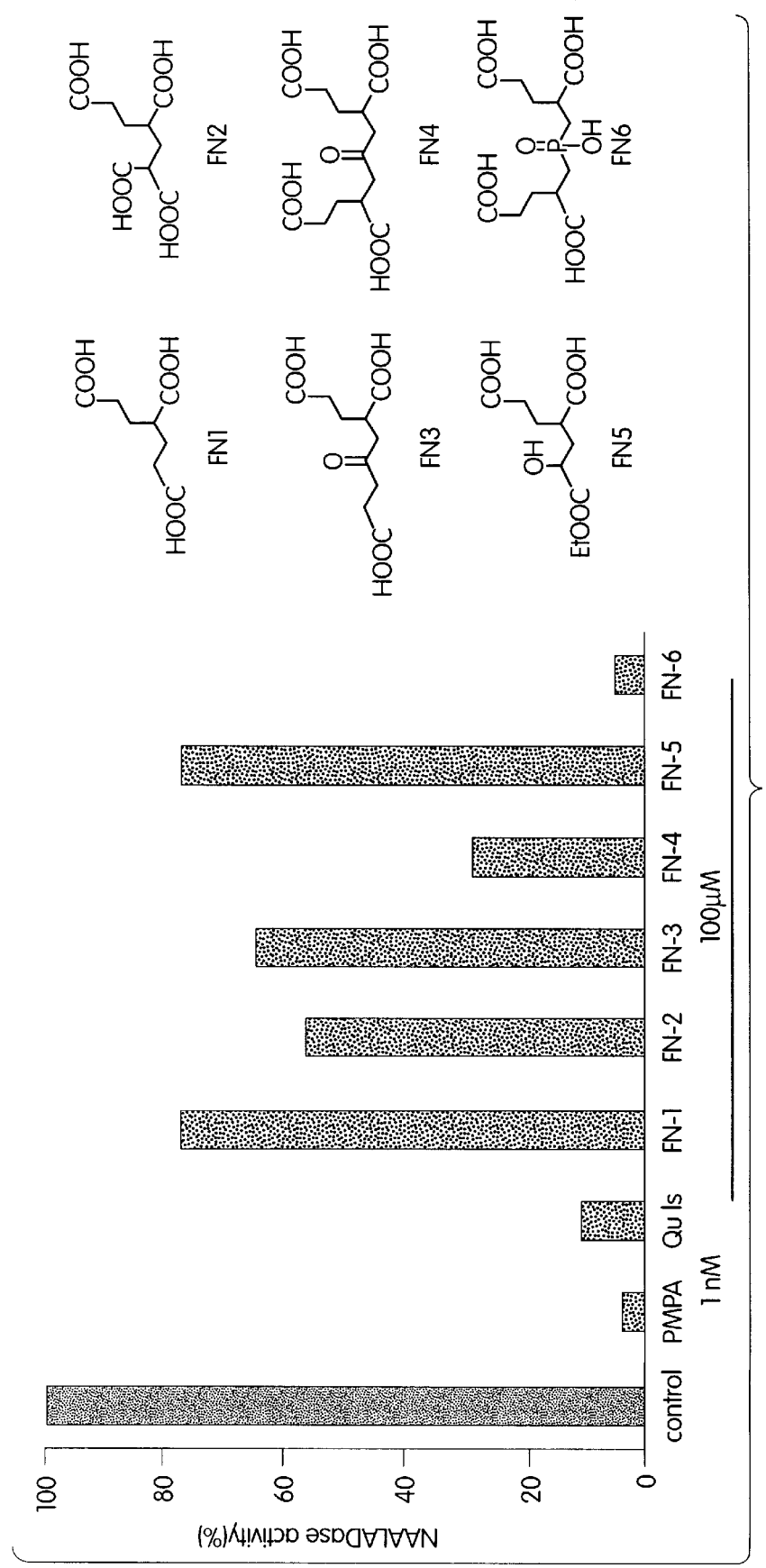
FIG. 2 depicts the effects of six compounds of the present invention on the activity of NAALADase.
Figure 3:
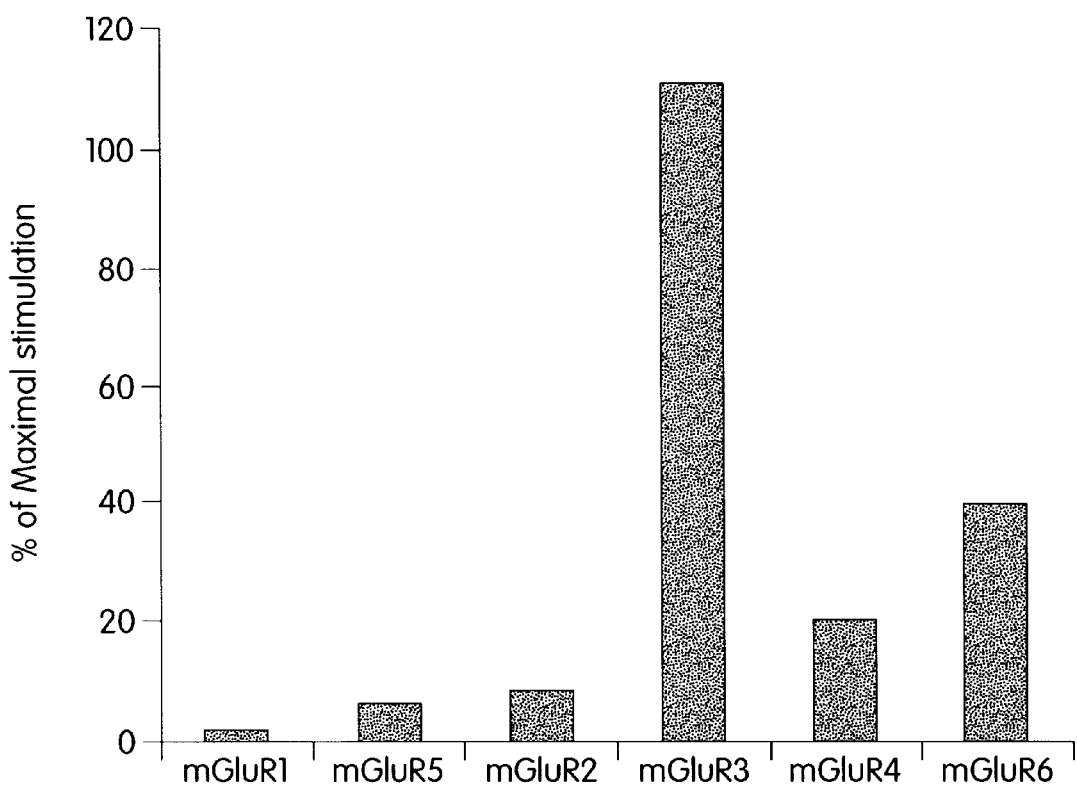
FIG. 3 depicts the effect of a compound of the present invention at six subtypes of metabotropic glutamate receptors (mGluRs).
Figure 4:
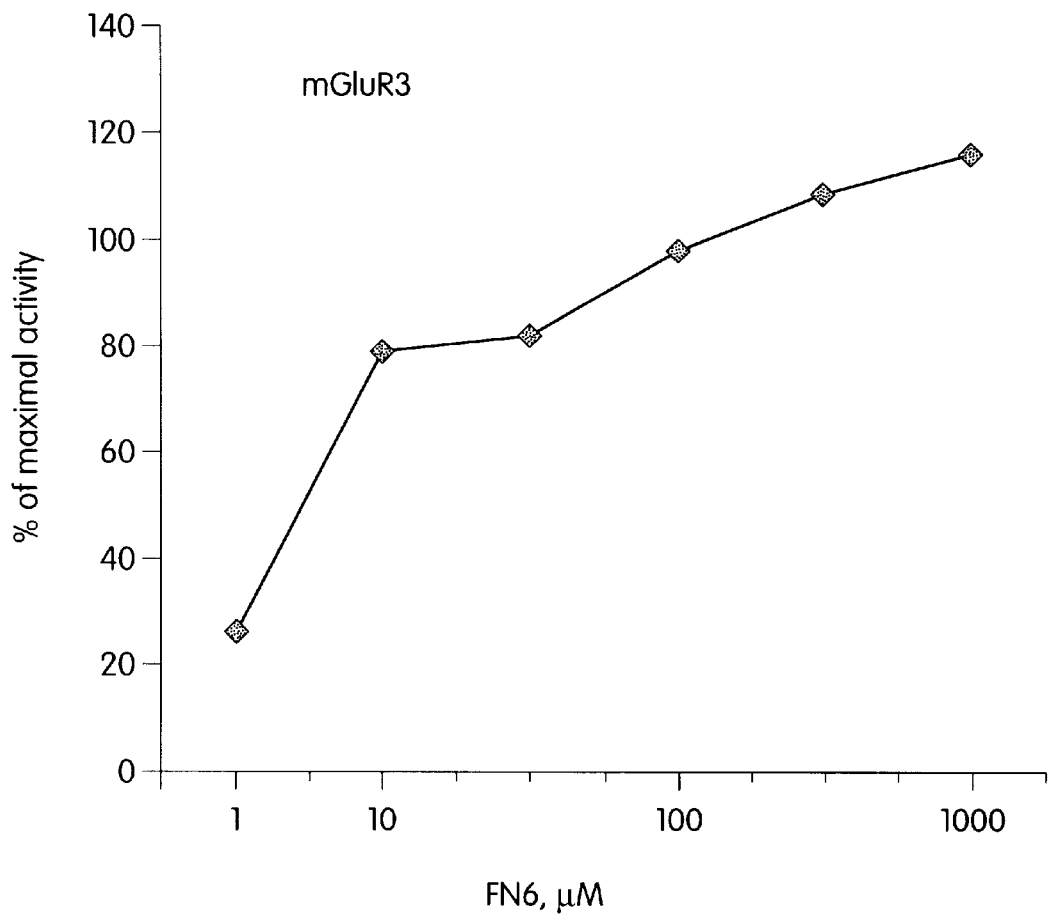
FIG. 4 depicts the effect of a compound of the present invention at a single subtype of metabotropic glutamate receptor.
Figure 5:
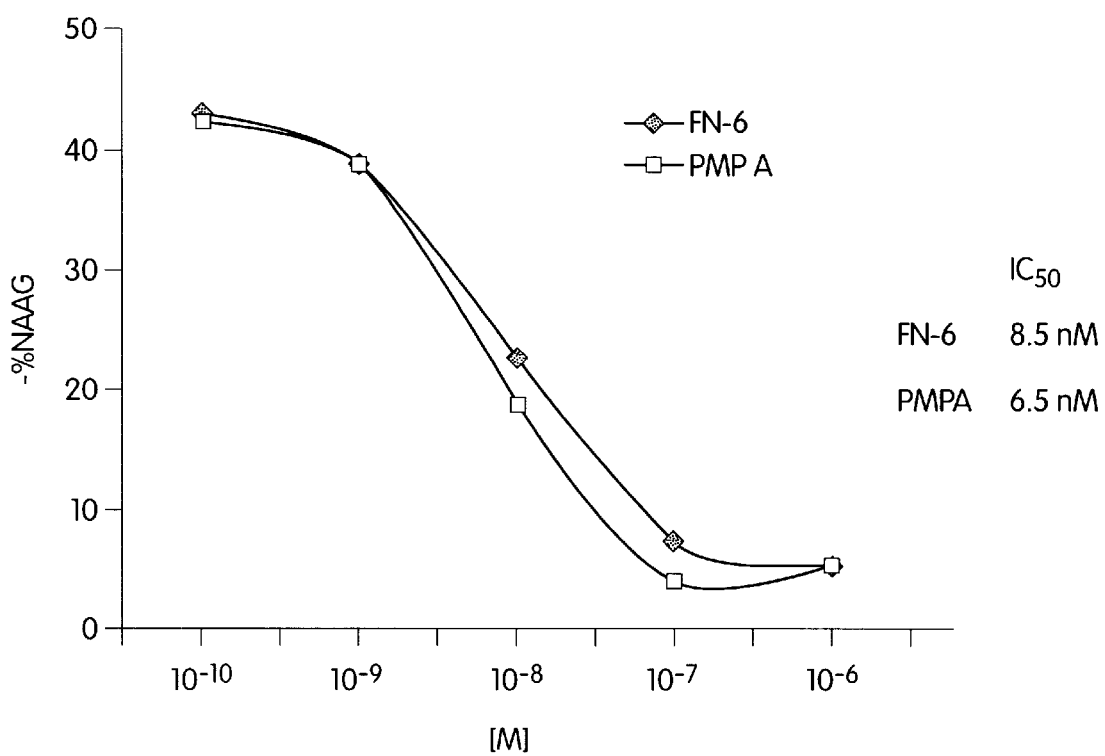
FIG. 5 depicts the effects of a compound of the present invention and 2-(phosphomethyl)pentanedioic acid (PMPA) on the activity of NAAG peptidase in rat brain membranes.
Figure 6:
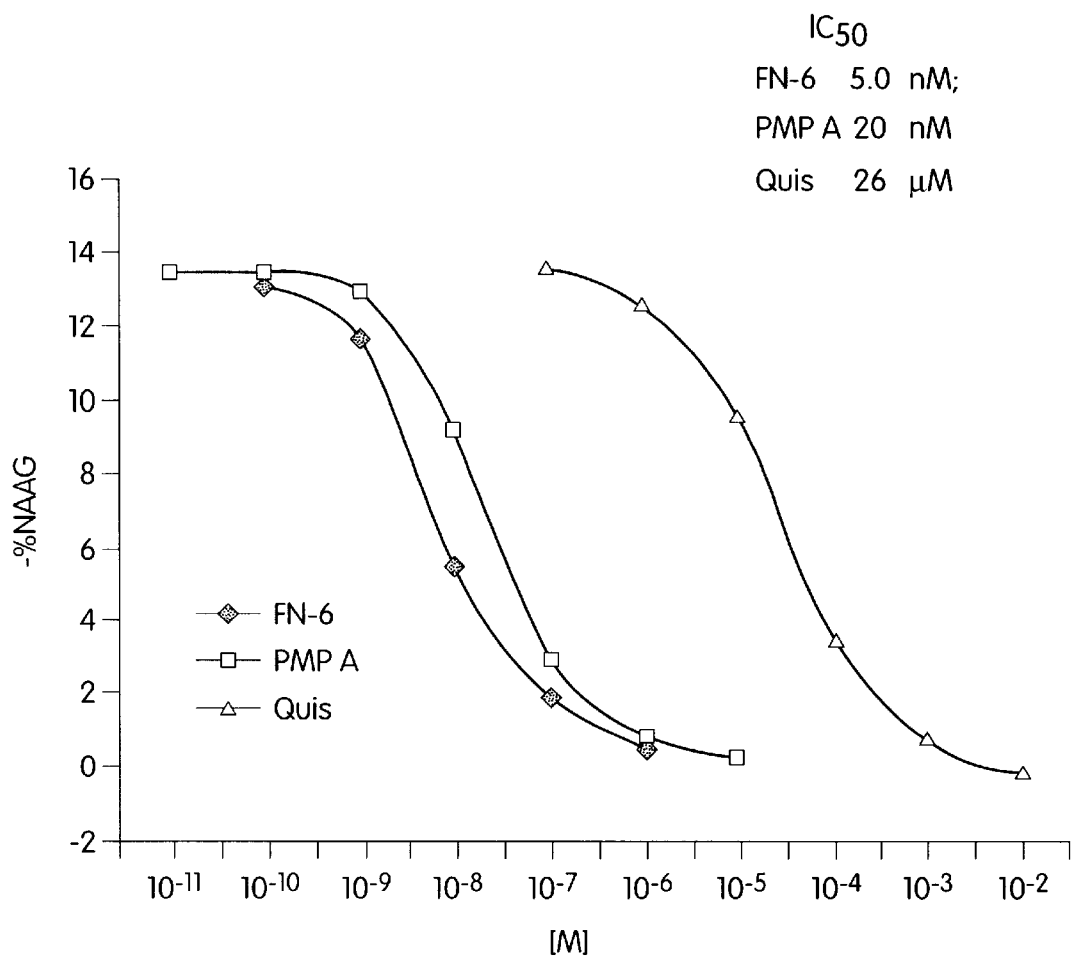
FIG. 6 depicts the effects of a compound of the present invention, PMPA, and Quis on the activity of rat NAAG peptidase.
Figure 7:
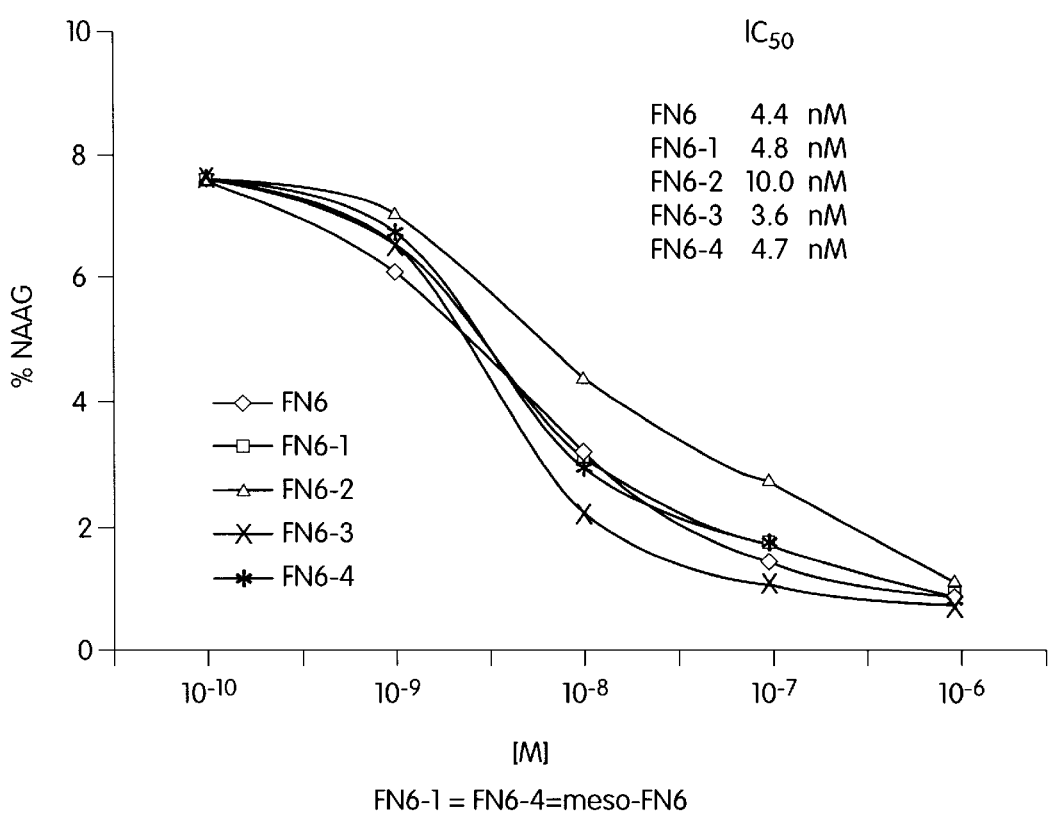
FIG. 7 depicts the effects of five compounds of the present invention on the activity of rat NAAG peptidasee
Figure 8:
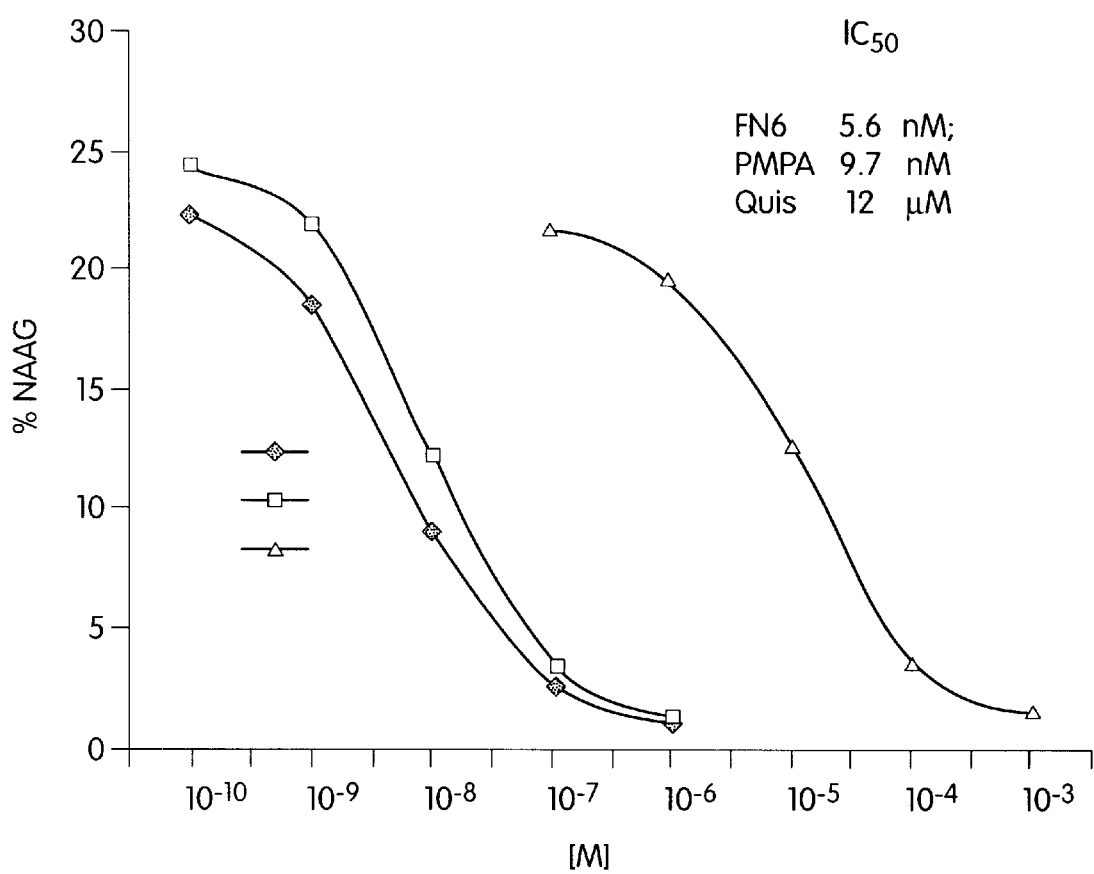
FIG. 8 depicts the effects of a compound of the present invention, PMPA, and Quis on the activity of prostate specific membrane antigen (PMSA).
Figure 9:
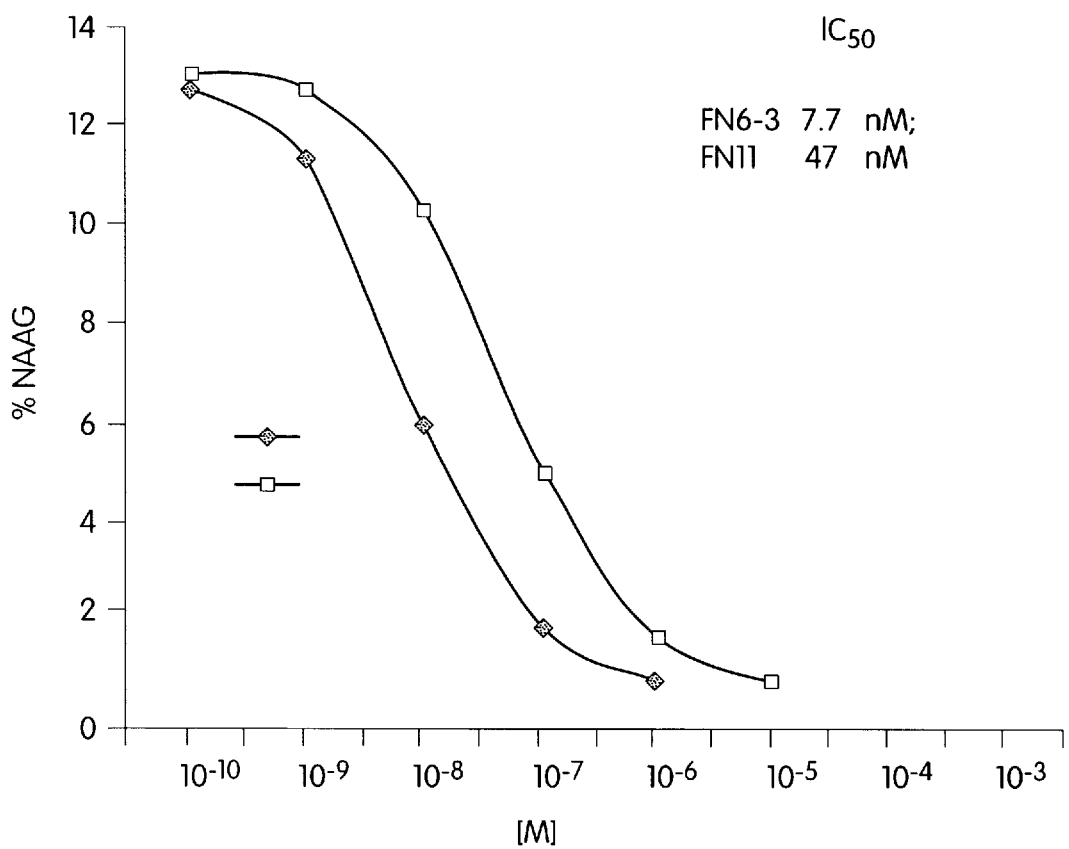
FIG. 9 depicts the effects of two compounds of the present invention on the activity of rat NAAG peptidase.

To date, all of the commonly used agonist and antagonists employed in biological studies of the mGluRs are amino acids, often embodying a structurally rigidified glutamate-like core [Neuropharmacology, 36, 1–11 (1997); Neuropharmacology 37, 1–12 (1998); Neuropharmacology 35, 1661–1672 (1996); J. Med. Chem. 38, 1417 (1995); J. Med. Chem. 41, 347 (1998); Current Pharmaceutical Design, 1, 355 (1995)] During our efforts to identify potent and selective ligands acting at these receptors, we have discovered mGluR$_3$ selective agonists that contains only acid groups.

Our studies began from the dipeptide N-acetyl-L-aspartate-L-glutamate (NAAG), a dipeptide that is quite abundant in the brain, and which is believed to act as a transmitter or co-transmitter in the central nervous system, much like glutamate itself. NAAG exhibits excitatory properties both in vitro and in vivo, but it is less active than glutamate and represents a storage form of glutamate. In studies using cell lines transfected with mGluR$_{1-6}$, NAAG was found to selectively activate the mGluR$_3$ receptor with an EC$_{50}$ value in the range of 65±20 μM [J. Neurochem. 69, 174(1997)]. Recently, a brain enzyme was identified that is specific for the cleavage of N-acetylated α-linked acidic dipeptides, and as a result this enzyme was named NAALADase [J. Biol. Chem., 1987, 262, 14498].

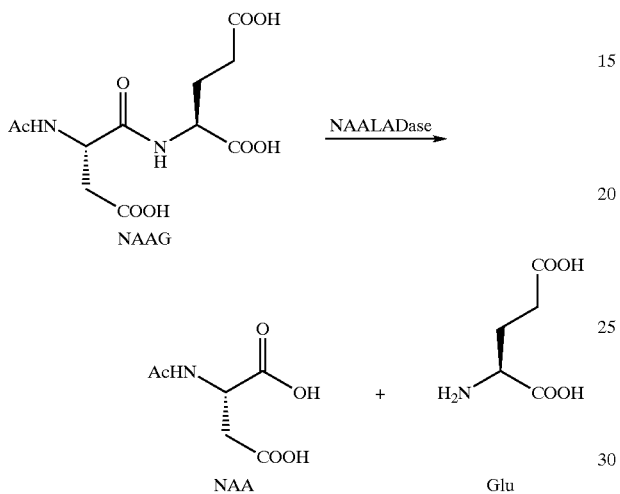

NAAG and NAALADase have been implicated in several pathological conditions relating to glutamate abnormalities and neurotoxicity. For example, it has been demonstrated that intra-hippocampal injections of NAAG elicit prolonged seizure activity [Proc. Natl. Acad. Sci. USA, 80(1983), 1116–1119]. It has also been reported that rats genetically prone to epileptic seizures demonstrate a persistent increase in their basal levels of NAALADase activity. [Brain Research, 593(1992), 140–143]. These results lend support to the hypothesis that the increased availability of synaptic glutamate elevates seizure susceptibility. As a consequence, it has been suggested that NAALADase inhibitors may provide effective anti-epileptic therapies.

NAAG and NAALADase have also been implicated in the pathogenesis of ALS (Amyotrophic Lateral Sclerosis) [Brain Research, 556 (1991), 151–156]. As such, NAALADase inhibitors might be clinically useful in curbing the progression of ALS if an increased metabolism of NAAG is responsible for alterations in the CSF levels of these acidic amino acids [see Ann. Neurol. 28(1990), 18–25].

Certain phosphonate analogs of NAAG, such as 2-(phosphonomethyl)-pentanedioic acid, have been reported to act as potent inhibitors of NAALADase [J. Med. Chem. 39, 619 (1996)]. Interestingly, while this compound was reported to show little in the way receptor activity, we found that it does in fact act as an agonist at mGluR$_3$.

Compounds of the Invention

Based upon this unexpected result, we were led to explore the activity of related analogs. As part of our design strategy, we decided to explore the activity of NAAG-like analogs that were missing the amide bond present between the Asp and Glu residue, (the standard ketomethylene type substitution), but also from which the N-acetyl group was deleted, as this particular group was reported not to be an absolute requirement for NAALADase activity.

Accordingly, a series of compounds was prepared and studied for mGluR activity. Of the compounds synthesized, the compound comprised of an acetone moiety flanked by the two pentanedioic acid groups (A) proved to be interesting, as it retained significant mGluR$_3$ activity.

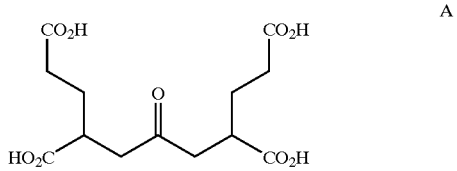

A

Based on this observation, we also chose to explore the activity of compounds in which the central carbonyl group of A was replaced by P(O)OH, CHOH, O, S, SO, SO$_2$, and R$_3$CHOH with the idea that this compound might act not only as an mGluR$_3$ selective ligand, but that it might also function as a NAALADase inhibitor. The phosphorous compound (B) was particularly potent as a NAALADase inhibitor, with an IC$_{50}$ of 4 nM. Additional data on the new compounds are provided herein.

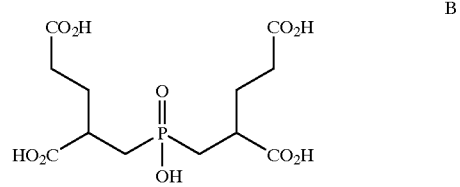

B

In certain embodiments, the compounds of the present invention are represented by generalized structure 1:

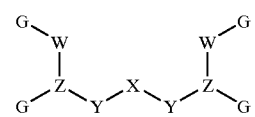

1 wherein

X is selected from the group consisting of —C(O)—, —C(S)—, —P(O)(OR)—, —P(O)(NR$_2$)—, —P(NR)(OR)—, —P(NR)(NR$_2$)—, O, S, —S(O)—, —S(O)$_2$—, Se, —Se(O)—, —Se(O)$_2$—, —C(R)(OR)—, —C(R)(SR)—, —C(NR)—, —NR(O)—, and —N(OR)—;

Y is selected, independently for each occurrence, from the group consisting of (CR$_2$)$_n$, (PR)$_n$, and a bond;

Z is selected, independently for each occurrence, from the group consisting of C(R), C(NR$_2$), C(NHacyl), N, and P;

W is selected, independently for each occurrence, from the group consisting of (CR$_2$)$_m$, (NR)$_m$, (PR)$_m$, and a bond;

G is selected, independently for each occurrence, from the group consisting of —COOH, —C(O)NHOH, —C(O)NH$_2$, —C(S)SH, —SO$_3$H, —SO$_2$H, —SOH, —SeO$_3$H, —SeO$_2$H, —SeOH, —S(O)$_2$NH$_2$, —P(O)(OH)$_2$, and —P(OH)$_2$;

R is selected, independently for each occurrence, from the group consisting of H, alkyl, heteroalkyl, aryl, heteroaryl, and aralkyl; and also including a negative charge for instances of R bonded to a heteroatom,: and m and n are integers selected, independently for each occurrence, from the range 0 to 3 inclusive.

In certain embodiments, the compounds of the present invention are represented by generalized structure 1 and the attendant definitions, wherein X is selected from the group consisting of —C(O)—, —C(S)—, —C(NR)—, —C(R)(OR)—, —C(R)(SR)—, —P(Q)(OR)—, —P(O)(N$_2$)—, —P(NR)(OR)—, and —P(NR)(NR$_2$)—.

In certain embodiments, the compounds of the present invention are represented by generalized structure 1 and the attendant definitions, wherein X is selected from the group consisting of —P(O)(OR)—, and —P(O)(NR$_2$)—.

In certain embodiments, the compounds of the present invention are represented by generalized structure 1 and the attendant definitions, wherein Y is (CR$_2$)$_n$.

In certain embodiments, the compounds of the present invention are represented by generalized structure 1 and the attendant definitions, wherein Y is (CR$_2$)$_n$; and n is 1.

In certain embodiments, the compounds of the present invention are represented by generalized structure 1 and the attendant definitions, wherein Z is selected, independently for each occurrence, from the group consisting of C(R), C(NR$_2$), and C(NHacyl).

In certain embodiments, the compounds of the present invention are represented by generalized structure 1 and the attendant definitions, wherein Z is C(R).

In certain embodiments, the compounds of the present invention are represented by generalized structure 1 and the attendant definitions, wherein W is (CR$_2$)$_m$.

In certain embodiments, the compounds of the present invention are represented by generalized structure 1 and the attendant definitions, wherein W is (CR$_2$)$_m$; and m is 2.

In certain embodiments, the compounds of the present invention are represented by generalized structure 1 and the attendant definitions, wherein G is selected, independently for each occurrence, from the group consisting of —COOH, —C(O)NHOH, —C(O)NH$_2$, —SO$_3$H, —SO$_2$H, —S(O)$_2$NH$_2$, and —P(O)(OH)$_2$.

In certain embodiments, the compounds of the present invention are represented by generalized structure 1 and the attendant definitions, wherein G is selected, independently for each occurrence, from the group consisting of —COOH, —C(O)NHOH, —SO$_3$H, and —P(O)(OH)$_2$.

In certain embodiments, the compounds of the present invention are represented by generalized structure 1 and the attendant definitions, wherein G is selected, independently for each occurrence, from the group consisting of —COOH, and —C(O)NHOH.

In certain embodiments, the compounds of the present invention are represented by generalized structure 1 and the attendant definitions, wherein G is —COOH.

In certain embodiments, the compounds of the present invention are represented by generalized structure 1 and the attendant definitions, wherein m and n are integers selected, independently for each occurrence, from the range 1 to 2 inclusive.

In certain embodiments, the compounds of the present invention are represented by generalized structure 1 and the attendant definitions, wherein X is selected from the group consisting of —C(O)—, —C(S)—, —C(NR)—, —C(R)(OR)—, —C(R)(SR)—, —P(O)(OR)—, —P(O)(NR$_2$)—, —P(NR)(OR)—, and —P(NR)(NR$_2$)—; and Y is (CR$_2$)$_n$.

In certain embodiments, the compounds of the present invention are represented by generalized structure 1 and the attendant definitions, wherein X is selected from the group consisting of —C(O)—, —C(S)—, —C(NR)—, —C(R)(OR)—, —C(R)(SR)—, —P(O)(OR)—, —P(O)(NR$_2$)—, —P(NR)(OR)—, and —P(NR)(NR$_2$)—; Y is (CR$_2$)$_n$; and Z is selected, independently for each occurrence, from the group consisting of C(R), C(NR$_2$), and C(NHacyl).

In certain embodiments, the compounds of the present invention are represented by generalized structure 1 and the attendant definitions, wherein X is selected from the group consisting of —C(O)—, —C(S)—, —C(NR)—, —C(R)(OR)—, —C(R)(SR)—, —P(O)(OR)—, —P(O)(NR$_2$)—, —P(NR)(OR)—, and —P(NR)(NR$_2$)—; Y is (CR$_2$)$_n$; Z is selected, independently for each occurrence, from the group consisting of C(R), C(NR$_2$), and C(NHacyl); and W is (CR$_2$)$_m$.

In certain embodiments, the compounds of the present invention are represented by generalized structure 1 and the attendant definitions, wherein X is selected from the group consisting of —C(O)—, —C(S)—, —C(NR)—, —C(R)(OR)—, —C(R)(SR)—, —P(O)(OR)—, —P(O)(NR$_2$)—, —P(NR)(OR)—, and —P(NR)(NR2)—; Y is (CR$_2$)$_n$; Z is selected, independently for each occurrence, from the group consisting of C(R), C(NR$_2$), and C(NHacyl); W is (CR$_2$)$_m$; and G is selected, independently for each occurrence, from the group consisting of —COOH, —C(O)NHOH, —C(O)NH$_2$, —SO$_3$H, —SO$_2$H, —S(O)2NH$_2$, and —P(O)(OH)$_2$.

In certain embodiments, the compounds of the present invention are represented by generalized structure 1 and the attendant definitions, wherein X is selected from the group consisting of —C(O)—, —C(S)—, —C(NR)—, —C(R)(OR)—, —C(R)(SR)—, —P(O)(OR)—, —P(O)(NR$_2$)—, —P(NR)(OR)—, and —P(NR)(NR$_2$)—; Y is (CR$_2$)$_n$; Z is selected, independently for each occurrence, from the group consisting of C(R), C(NR$_2$), and C(NHacyl); W is (CR$_2$)$_m$; G is selected, independently for each occurrence, from the group consisting of —COOH, —C(O)NHOH, —C(O)NH$_2$, —SO$_3$H, —SO$_2$H, —S(O)2NH$_2$, and —P(O)(OH)$_2$; and m and n are integers selected, independently for each occurrence, from the range 1 to 2 inclusive.

In certain embodiments, the compounds of the present invention are represented by generalized structure 1 and the attendant definitions, wherein X is selected from the group consisting of —P(O)(OR)—, and —P(O)(NR$_2$)—; and Y is (CR$_2$)$_n$.

In certain embodiments, the compounds of the present invention are represented by generalized structure 1 and the attendant definitions, wherein X is selected from the group consisting of —P(O)(OR)—, and —P(O)(NR$_2$)—; Y is (CR$_2$)$_n$; and Z is C(R).

In certain embodiments, the compounds of the present invention are represented by generalized structure 1 and the attendant definitions, wherein X is selected from the group consisting of —P(O)(OR)—, and —P(O)(NR2)—; Y is (CR$_2$)$_n$; Z is C(R); and W is (CR$_2$)$_m$.

In certain embodiments, the compounds of the present invention are represented by generalized structure 1 and the attendant definitions, wherein X is selected from the group consisting of —P(O)(OR)—, and —P(O)(NR$_2$)—; Y is (CR$_2$)$_n$; Z is C(R); W is (CR$_2$)$_m$, and G is selected, independently for each occurrence, from the group consisting of —COOH, and —C(O)NHOH.

In certain embodiments, the compounds of the present invention are represented by generalized structure 1 and the attendant definitions, wherein X is selected from the group consisting of —P(O)(OR)—, and —P(O)(NR$_2$)—; Y is (CR$_2$)$_n$; Z is C(R); W is (CR$_2$)$_m$; G is selected, independently for each occurrence, from the group consisting of —COOH, and —C(O)NHOH; and m and n are integers selected, independently for each occurrence, from the range 1 to 2 inclusive.

In certain embodiments, a compound of the present invention is represented by generalized structure 1 and the attendant definitions, wherein the compound is a ligand for a metabotropic glutamate receptor.

In certain embodiments, a compound of the present invention is represented by generalized structure 1 and the attendant definitions, wherein the compound is an agonist of a metabotropic glutamate receptor.

In certain embodiments, a compound of the present invention is represented by generalized structure 1 and the attendant definitions, wherein the compound is an antagonist of a metabotropic glutamate receptor.

In certain embodiments, a compound of the present invention is represented by generalized structure 1 and the attendant definitions, wherein the compound is a ligand for a single subtype of metabotropic glutamate receptor.

In certain embodiments, a compound of the present invention is represented by generalized structure 1 and the attendant definitions, wherein the compound is an agonist of a single subtype of metabotropic glutamate receptor.

In certain embodiments, a compound of the present invention is represented by generalized structure 1 and the attendant definitions, wherein the compound is an antagonist of a single subtype of metabotropic glutamate receptor.

In certain embodiments, a compound of the present invention is represented by generalized structure 1 and the attendant definitions, wherein the compound is an inhibitor of NAALADase.

In certain embodiments, the compounds of the present invention are represented by generalized structure 2:

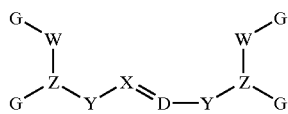

wherein
X is selected from the group consisting of —C(R)=, —C(OR)=, —C(SR)=, and —C(NR)=;
Y is selected, independently for each occurrence, from the group consisting of $(CR_2)_n$, $(NR)_n$, $(PR)_n$, and a bond;
D is selected from the group consisting of =C(R)—, =N—, and =P—;
Z is selected, independently for each occurrence, from the group consisting of C(R), $C(NR_2)$, C(NHacyl), N, and P;
W is selected, independently for each occurrence, from the group consisting of $(CR_2)_m$, $(NR)_m$, $(PR)_m$, and a bond;
G is selected, independently for each occurrence, from the group consisting of —COOH, —C(O)NHOH, —C(O)$NH_2$, —C(S)SH, —$SO_3H$, —$SO_2H$, —SOH, —$SeO_3H$, —$SeO_2H$, —SeOH, —S(O)$_2NH_2$, —P(O)(OH)$_2$, and —P(OH)$_2$;
R is selected, independently for each occurrence, from the group consisting of H, alkyl, heteroalkyl, aryl, heteroaryl, and aralkyl; and also including a negative charge for instances of R bonded to a heteroatom; and
m and n are integers selected, independently for each occurrence, from the range 0 to 3 inclusive.

In certain embodiments, the compounds of the present invention are represented by generalized structure 2 and the attendant definitions, wherein X is selected from the group consisting of —C(OR)=, and —C(SR)=.

In certain embodiments, the compounds of the present invention are represented by generalized structure 2 and the attendant definitions, wherein X is —C(SR)=.

In certain embodiments, the compounds of the present invention are represented by generalized structure 2 and the attendant definitions, wherein Y is $(CR_2)_n$.

In certain embodiments, the compounds of the present invention are represented by generalized structure 2 and the attendant definitions, wherein the instance of Y bonded to D is a bond.

In certain embodiments, the compounds of the present invention are represented by generalized structure 2 and the attendant definitions, wherein D is =C(R)—.

In certain embodiments, the compounds of the present invention are represented by generalized structure 2 and the attendant definitions, wherein D is =C(R)—; and the instance of Y bonded to D is a bond.

In certain embodiments, the compounds of the present invention are represented by generalized structure 2 and the attendant definitions, wherein Z is selected, independently for each occurrence, from the group consisting of C(R), $C(NR_2)$, and C(NHacyl).

In certain embodiments, the compounds of the present invention are represented by generalized structure 2 and the attendant definitions, wherein Z is C(R).

In certain embodiments, the compounds of the present invention are represented by generalized structure 2 and the attendant definitions, wherein W is $(CR_2)_m$.

In certain embodiments, the compounds of the present invention are represented by generalized structure 2 and the attendant definitions, wherein W is $(CR_2)_m$; and m is 2.

In certain embodiments, the compounds of the present invention are represented by generalized structure 2 and the attendant definitions, wherein G is selected, independently for each occurrence, from the group consisting of —COOH, —C(O)NHOH, —C(O)$NH_2$, —$SO_3H$, —$SO_2H$, —S(O)$_2NH_2$, and —P(O)(OH)$_2$.

In certain embodiments, the compounds of the present invention are represented by generalized structure 2 and the attendant definitions, wherein G is selected, independently for each occurrence, from the group consisting of —COOH, —C(O)NHOH, —$SO_3H$, and —P(O)(OH)$_2$.

In certain embodiments, the compounds of the present invention are represented by generalized structure 2 and the attendant definitions, wherein G is selected, independently for each occurrence, from the group consisting of —COOH, and —C(O)NHOH.

In certain embodiments, the compounds of the present invention are represented by generalized structure 2 and the attendant definitions, wherein G is —COOH.

In certain embodiments, the compounds of the present invention are represented by generalized structure 2 and the attendant definitions, wherein m and n are independently for each occurrence 0, 1, or 2.

In certain embodiments, the compounds of the present invention are represented by generalized structure 2 and the attendant definitions, wherein X is selected from the group consisting of —C(OR)=, and —C(SR)=; and Y is $(CR_2)_n$.

In certain embodiments, the compounds of the present invention are represented by generalized structure 2 and the attendant definitions, wherein X is selected from the group consisting of —C(OR)=, and —C(SR)=; and D is =C(R)—.

In certain embodiments, the compounds of the present invention are represented by generalized structure 2 and the attendant definitions, wherein X is selected from the group consisting of —C(OR)=, and —C(SR)=; D is =C(R)—; and the instance of Y bonded to D is a bond.

In certain embodiments, the compounds of the present invention are represented by generalized structure 2 and the attendant definitions, wherein X is selected from the group consisting of —C(OR)=, and —C(SR)=; Y is $(CR_2)_n$; and Z is selected, independently for each occurrence, from the group consisting of C(R), $C(NR_2)$, and C(NHacyl).

In certain embodiments, the compounds of the present invention are represented by generalized structure 2 and the attendant definitions, wherein X is selected from the group consisting of —C(OR)=, and —C(SR)=; Y is $(CR_2)_n$; Z is selected, independently for each occurrence, from the group consisting of C(R), $C(NR_2)$, and C(NHacyl) and W is $(CR_2)_m$.

In certain embodiments, the compounds of the present invention are represented by generalized structure 2 and the attendant definitions, wherein X is selected from the group consisting of —C(OR)=, and —C(SR)=; Y is $(CR_2)_n$; Z is selected, independently for each occurrence, from the group consisting of C(R), $C(NR_2)$, and C(NHacyl); W is $(CR_2)_m$; and G is selected, independently for each occurrence, from the group consisting of —COOH, —C(O)NHOH, —C(O)$NH_2$, —$SO_3H$, —$SO_2H$, —$S(O)_2NH_2$, and —$P(O)(OH)_2$.

In certain embodiments, the compounds of the present invention are represented by generalized structure 2 and the attendant definitions, wherein X is selected from the group consisting of —C(OR)=, and —C(SR)=; Y is $(CR_2)_n$; Z is selected, independently for each occurrence, from the group consisting of C(R), $C(NR_2)$, and C(NHacyl); W is $(CR_2)_m$; G is selected, independently for each occurrence, from the group consisting of —COOH, —C(O)NHOH, —C(O)$NH_2$, —$SO_3H$, —$SO_2H$, —$S(O)_2NH_2$, and —$P(O)(OH)_2$; and m and n are independently for each occurrence 0, 1, or 2.

In certain embodiments, the compounds of the present invention are represented by generalized structure 2 and the attendant definitions, wherein X is —C(SR)=; and Y is $(CR_2)_n$.

In certain embodiments, the compounds of the present invention are represented by generalized structure 2 and the attendant definitions, wherein X is —C(SR)=; and D is =C(R)—.

In certain embodiments, the compounds of the present invention are represented by generalized structure 2 and the attendant definitions, wherein X is —C(SR)=; D is =C(R)—; and the instance of Y bonded to D is a bond.

In certain embodiments, the compounds of the present invention are represented by generalized structure 2 and the attendant definitions, wherein X is —C(SR)=; Y is $(CR_2)_n$; and Z is C(R).

In certain embodiments, the compounds of the present invention are represented by generalized structure 2 and the attendant definitions, wherein X is —C(SR)=; Y is $(CR_2)_n$; Z is C(R); and W is $(CR_2)_m$.

In certain embodiments, the compounds of the present invention are represented by generalized structure 2 and the attendant definitions, wherein X is —C(SR)=; Y is $(CR_2)_n$; Z is C(R); W is $(CR_2)_m$; and G is selected, independently for each occurrence, from the group consisting of —COOH, and —C(O)NHOH.

In certain embodiments, the compounds of the present invention are represented by generalized structure 2 and the attendant definitions, wherein X is —C(SR)=; Y is $(CR_2)_n$; Z is C(R); W is $(CR_2)_m$; G is selected, independently for each occurrence, from the group consisting of —COOH, and —C(O)NHOH; and m and n are independently for each occurrence 0, 1, or 2.

In certain embodiments, a compound of the present invention is represented by generalized structure 2 and the attendant definitions, wherein the compound is a ligand for a metabotropic glutamate receptor.

In certain embodiments, a compound of the present invention is represented by generalized structure 2 and the attendant definitions, wherein the compound is an agonist of a metabotropic glutamate receptor.

In certain embodiments, a compound of the present invention is represented by generalized structure 2 and the attendant definitions, wherein the compound is an antagonist of a metabotropic glutamate receptor.

In certain embodiments, a compound of the present invention is represented by generalized structure 2 and the attendant definitions, wherein the compound is a ligand for a single subtype of metabotropic glutamate receptor.

In certain embodiments, a compound of the present invention is represented by generalized structure 2 and the attendant definitions, wherein the compound is an agonist of a single subtype of metabotropic glutamate receptor.

In certain embodiments, a compound of the present invention is represented by generalized structure 2 and the attendant definitions, wherein the compound is an antagonist of a single subtype of metabotropic glutamate receptor.

In certain embodiments, a compound of the present invention is represented by generalized structure 2 and the attendant definitions, wherein the compound is an inhibitor of NAALADase.

Another aspect of the present invention relates to methods of treating ischemia, in particular global and focal ischemia, using compositions which inhibit N-Acetylated alpha-Linked Acidic Dipeptidase (NAALADase) enzyme activity in humans and warm-blooded animals. Certain compounds represented by generalized structures 1 and 2 are inhibitors of NAALADase. Those of ordinary skill in the art will be able to ascertain using no more than routine experimentation which compounds of the present invention are antagonists of NAALADase.

NAALADase is an enzyme which is a membrane-bound metalloprotease that hydrolyzes the dipeptide, N-acetyl-L-aspartate-L-glutamate (NAAG) to yield glutamate and N-acetylaspartate. The methods of the present invention include using compositions containing phosphinic acid derivatives that inhibit NAALADase enzyme activity and which have been found useful for the treatment of ischemia. The amino acid L-glutamate is a neurotransmitter that mediates fast neuronal excitation in a majority of synapses in the central nervous system (CNS). Once released into the synapse, L-glutamate can stimulate the N-methyl-D-aspartate (NMDA) receptor, a subtype of an excitatory amino acid receptor. It has been discovered that excessive activation of the NMDA receptor has been implicated in a variety of acute as well as chronic neurophathological processes such as ischemia, epilepsy and Huntington's disease. Thus, considerable effort has focused on finding novel therapeutic agents to antagonize the postsynaptic effects of L-glutamate medicated through the NMDA receptor.

Certain embodiments of the present invention consist of a method for treating ischemia which comprises the step of administering to an animal suffering from an ischemia a NAALADase inhibitor and pharmaceutically acceptable carrier for said NAALADase inhibitor. In methods of treating stroke, particularly acute ischemic stroke, and global ischemia caused by drowning, head trauma and so forth, a NAALADase inhibitor can be co-administered with one or more agents active in reducing the risk of stroke, such as aspirin or ticlopidine (preferably ticlopidine, which has been demonstrated to reduce the risk of a second ischemic event). Co-administration can be in the form of a single formulation (combining, for example, a NAALADase inhibitor and ticlopidine with pharmaceutically acceptable excipients, optionally segregating the two active ingredients in different excipientmixtures designed to independently control their respective release rates and durations) or by independent administration of separate formulations containing the active agents, If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The NAALADase inhibitors of this invention are generally administered as a pharmaceutical composition which comprises a pharmaceutical excipient in combination with the inhibitor. The level of the drug in a formulation can vary within the full range employed by those skilled in the art, namely, from about 0.01 percent weight (% w) to about 99.99% w of the drug based on the total formulation and about 0.01% w to 99.99% w excipient. Preferably, the formulation will be about 3.5 to 60% by weight of the NAALADase inhibitor, with the rest being suitable pharmaceutically excipients.

Definitions

For convenience, before further description of the present invention, certain terms employed in the specification, examples, and appended claims are collected here.

"NAALADase" as used herein refers to N-Acetylated Alpha-Linked Acidic Dipeptidase. The enzyme was originally named for it's substrate specificity for hydrolyzing N-acetylated alpha-linked acidic dipeptides. Currently, it is known that the enzyme has a broader range of substrate specificity than originally discovered, particularly that the enzyme does not require N-acetylation or alpha-linkage. Thus, as used herein "NAALADase" encompasses other names used in the literature such as NAAG hydrolyzing enzyme and NAALA dipeptidase.

The term "inhibition", in the context of enzyme inhibition, relates to reversible enzyme inhibition such as competitive, uncompetitive, and noncompetitive inhibition. This can be experimentally distinguished by the effects of the inhibitor on the reaction kinetics of the enzyme, which may be analyzed in terms of the basic Michaelis-Menten rate equation. Competitive inhibition occurs when the inhibitor can combine with the free enzyme in such a way that it competes with the normal substrate for binding at the active site. A competitive inhibitor reacts reversibly with the enzyme to form an enzyme-inhibitor complex [EI]. Following the Michaelis-Menten formalism, we can define the inhibitor constant, K[i], as the dissociation constant of the enzyme-inhibitor complex. Thus, in accordance with the above and as used herein, K[i] is essentially a measurement of affinity between a molecule, and its receptor, or in relation to the present invention, between the present inventive compounds and the enzyme to be inhibited. It should be noted that IC50 is a related term used when defining the concentration or amount of a compound which is required to cause a 50% inhibition of the target enzyme.

The term "ischemia" relates to localized tissue anemia due to obstruction of the inflow of arterial blood. Global ischemia occurs under conditions in which blood flow to the entire brain ceases for a period of time, such as may result from cardiac arrest. Focal ischemia occurs under conditions in which a portion of the brain is deprived of its normal blood supply, such as may result from thromboembolytic occlusion of a cerebral vessel, traumatic head injury, edema, and brain tumors.

The term "nervous tissue" refers to the various components that make up the nervous system including neurons, neural support cells, glia, Schwann cells, vasculature contained within and supplying these structures, the central nervous system, the brain, the brain stem, the spinal cord, the junction of the central nervous system with the peripheral nervous system, the peripheral nervous system and allied structures.

The term "nervous function" refers to the various functions of the nervous system and its parts which are manifest in sensing the environment, awareness of it, homeostasis to it and interaction with it as shown, by example, in the ability to perform activities of daily living, work, cogitation and speech.

The term "nervous insults" refers to damage to nervous tissue which includes brain and nervous tissue damage and destruction, in whole or in part, and resultant morbidity, disability, neurologic deficia and death. Nervous insult can be from various origins including ischemia, hypoxia, cerebrovascular accident, metabolic, toxic, neurotoxic, trauma, surgery, iatrogenic, pressure, mass effect, hemorrhage, thermal, chemical, radiation, vasospasm, neurodegenerative disease, neurodegenerative process, infection, Parkinson's disease, amyotrophic lateral sclerosis, myelination/demyelination processes, epilepsy, cognitive disorders, glutamate abnormalities, and their secondary effects.

The term "glutamate abnormalities" refers to any condition, disease, or disorder that involves glutamate, and includes but is not limited to the nervous insults listed above.

The term "glutamate modulator" refers to any composition of matter, alone or in combination with another agent, which affects the level of glutamate in an animal, including a human being.

The term "neuroprotective" is an effect which reduces, arrests, or ameliorates nervous insult and is protective, resuscitative or revivative for nervous tissue that has suffered nervous insult.

The tern "treatment" refers to ally process, action, application, therapy, or the like, wherein an animal, including a human being, is subject to medical aid with the object of improving the animal's condition, directly or indirectly. The method of this invention for treating global ischemia comprises administering internally to a subject expected to be benefitted thereby with an effective amount of a NAALADase inhibitor. Doses of this isomer included in the present methods and pharmaceutical compositions are an efficacious, nontoxic quantity. Persons skilled in the art using routine clinical testing are able to determine optimum doses. The desired dose is administered to a subject from 1 to 6 or more times daily, orally, rectally, parenterally, or topically and may follow a higher initial amount administered as a bolus dose.

The term "nucleophile" is recognized in the art, and as used herein means a chemical moiety having a reactive pair of electrons.

The term "electrophile" is art-recognized and refers to chemical moieties which can accept a pair of electrons from a nucleophile as defined above. Electrophilic moieties useful in the method of the present invention include halides and sulfonates.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (s) constant. This well known constant is described in many references, for instance, J. March, *Advanced Organic Chemistry*, McGraw Hill Book Company, New York, (1977 edition) pp. 251–259.

The Hammett constant values are generally negative for electron donating groups (s[P]=−0.66 for NH$_2$) and positive for electron withdrawing groups (s[P]=0.78 for a nitro group), s[P] indicating para substitution. Exemplary electron-withdrawing groups include nitro, ketone, aldehyde, sulfonyl, trifluoromethyl, —CN, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has 10 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formyl, or a ketone), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In certain embodiments, a substituent designated herein as alkyl is a lower alkyl.

The term "heteroalkyl" as used herein means an alkyl group including or substituted with one or more heteroatoms.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*: this list is typically presented in a table entitled *Standard List of Abbreviations*. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle", as used herein, refers to an aromatic or non-aromatic ring in which each atom of the ring is carbon.

The term "heteroatom" as used herein means an atom of any element other than carbon or hydrogen. Preferred heteroatoms are nitrogen, oxygen, sulfur and phosphorous.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms "amine" and "amino" are art recognized and refer to both unsubstituted and substituted amines, e.g., a moiety that can be represented by the general formula:

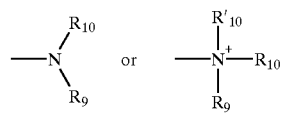

wherein R$_9$, R$_{10}$ and R'$_{10}$ each independently represent a hydrogen, an alkyl, an alkenyl, —(CH$_2$)$_m$—R$_8$, or R$_9$ and R$_{10}$ taken together with the N atom to which they are attached complete a heterocycle having from 4 to 8 atoms in the ring structure; R$_8$ represents an aryl, a cycloalkyl, a cycloalkenyl, a heterocycle or a polycycle; and m is zero or an integer in the range of 1 to 8. In preferred embodiments, only one of R$_9$ or R$_{10}$ can be a carbonyl, e.g., R$_9$, R$_{10}$ and the nitrogen together do not form an imide. In even more preferred embodiments, R$_9$ and R$_{10}$ (and optionally R'$_{10}$) each independently represent a hydrogen, an alkyl, an alkenyl, or —(CH$_2$)$_m$—R$_8$. Thus, the term "alkylamine" as used herein means an amine group, as defined above, having a substituted or unsubstituted alkyl attached thereto, i.e., at least one of R$_9$ and R$_{10}$ is an alkyl group.

The term "acylamino" is art-recognized and refers to a moiety that can be represented by the general formula:

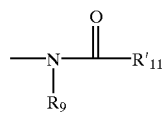

wherein R9 is as defined above, and R'$_{11}$ represents a hydrogen, an alkyl, an alkenyl or —(CH$_2$)$_m$—R$_8$, where m and R$_8$ are as defined above.

The term "amido" is art recognized as an amino-substituted carbonyl and includes a moiety that can be represented by the general formula:

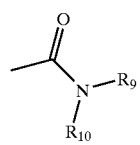

wherein R$_9$, R$_{10}$ are as defined above. Certain embodiments of the amide will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R$_8$, wherein m and R$_8$ are defined above. Representative alkylthio groups include methylthio, ethyl thio, and the like.

The term "carbonyl" is art recognized and includes such moieties as can be represented by the general formula:

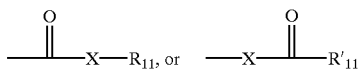

wherein X is a bond or represents an oxygen or a sulfur, and R$_{11}$ represents a hydrogen, an alkyl, an alkenyl, —(CH$_2$)$_m$—R$_8$ or a pharmaceutically acceptable salt, R'$_{11}$ represents a hydrogen, an alkyl, an alkenyl or —(CH$_2$)$_m$—R$_8$, where m and R$_8$ are as defined above. Where X is an oxygen and R$_{11}$ or R'$_{11}$ is not hydrogen, the formula represents an "ester". Where X is an oxygen, and R$_{11}$ is as defined above, the moiety is referred to herein as a carboxyl group, and particularly when R$_{11}$ is a hydrogen, the formula represents a "carboxylic acid". Where X is an oxygen, and R'$_{11}$ is hydrogen, the formula represents a "formate". In general, where the oxygen atom of the above formula is replaced by sulfur, the formula represents a "thiolcarbonyl" group. Where X is a sulfur and R$_{11}$ or R'$_{11}$ is not hydrogen, the formula represents a "thiolester." Where X is a sulfur and R$_{11}$ is hydrogen, the formula represents a "thiolcarboxylic acid." Where X is a sulfur and R$_{11}$' is hydrogen, the formula represents a "thiolformate." On the other hand, where X is a bond, and R$_{11}$ is not hydrogen, the above formula represents a "ketone" group. Where X is a bond, and R$_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH$_2$)$_m$—R$_8$, where m and R$_8$ are described above.

The term "sulfonate" is art recognized and includes a moiety that can be represented by the general formula:

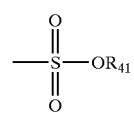

in which R$_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "sulfate" is art recognized and includes a moiety that can be represented by the general formula:

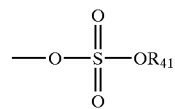

in which R$_{41}$ is as defined above.

The term "sulfonamido" is art recognized and includes a moiety that can be represented by the general formula:

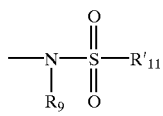

in which $R_9$ and $R'_{11}$ are as defined above.

The term "sulfamoyl" is art-recognized and includes a moiety that can be represented by the general formula:

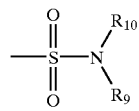

in which $R_9$ and $R_{10}$ are as defined above.

The terms "sulfoxido" or "sulfinyl", as used herein, refers to a moiety that can be represented by the general formula:

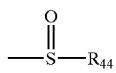

in which $R_{44}$ is selected from the group consisting of hydrogen, alkyl, alkenyl, alkynyl, cycloalkyl, heterocyclyl, aralkyl, or aryl.

A "phosphoryl" can in general be represented by the formula:

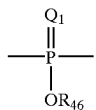

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

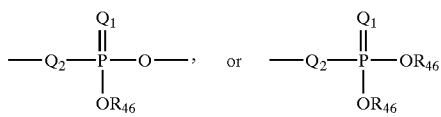

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "phosphoramidite" can be represented in the general formula:

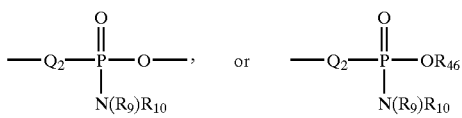

wherein $R_9$ and $R_{10}$ are as defined above, and $Q_2$ represents O, S or N.

A "phosphonamidite" can be represented in the general formula:

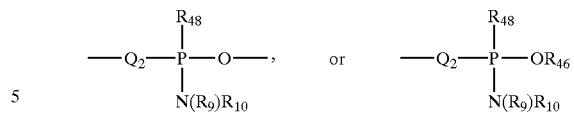

wherein $R_9$ and $R_{10}$ are as defined above, $Q_2$ represents O, S or N, and $R_{48}$ represents a lower alkyl or an aryl, $Q_2$ represents O, S or N.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_8$, m and $R_8$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. —Protective Groups in Organic Synthesis, $2^{nd}$ ed.; Wiley; New York, 1991).

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

A "polar solvent" means a solvent which has a dipole moment ($\epsilon$) of 2.9 or greater, such as DMF, THF, ethylene glycol dimethyl ether, DMSO, acetone, acetonitrile, methanol, ethanol, isopropanol, n-propanol, t-butanol or 2-methoxyethyl ether. Preferred solvents are DMF, diglyme, and acetonitrile.

An "aprotic solvent" means a solvent that is not a hydrogen bond donor. Examples of such solvents are acetonitrile, toluene, DMF, diglyme, THF or DMSO.

A "polar, aprotic solvent" means a solvent which has a dipole moment ($\epsilon$) of 2.9, and is not a hydrogen bond donor, for example DMF, acetonitrile, DMSO and THF.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmacutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1–19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmacutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Administration of the adenosine antagonists and agonists for use in the method of this invention can be via any of the accepted modes of administration. These methods include, but are not limited to, oral, parenteral, transdermal, intraarticular and otherwise systemic administration. Oral administration is preferred. The compounds are administered in a therapeutically effective amount either alone or in combination with a suitable pharmaceutically acceptable carrier or excipient.

Depending on the intended mode of administration, the adenosine antagonist or agonist of choice may be incorporated in any pharmaceutically acceptable dosage form, such as, for example, tablets, transdermal patches, pills, capsules, powders, liquids, suspensions, emulsions, aerosols or the like, preferably in unit dosage forms suitable for single administration of precise dosages, or sustained release dosage forms for continuous controlled administration. Preferably the dosage form will include a pharmaceutically acceptable excipient and, in addition, may contain other medicinal agents, pharmaceutical agents, carriers, adjuvants, and the like.

For solid dosage forms, non-toxic carriers include but are not limited to, for example, pharmaceutical grades of mannitol, lactose, starch, magnesium stearate, sodium saccharin, the polyalkylene glycols, talcum, cellulose, glucose, sucrose and magnesium carbonate. Liquid pharmaceutically administrable dosage forms can, for example, comprise a solution or suspension of an active adenosine agent and optional pharmaceutical adjuvants in a carrier, such as, for example, water, saline aqueous dextrose, glycerol, ethanol and the like, to thereby form a solution or suspension. If desired, the pharmaceutical composition to be administered may also contain minor amounts of non-toxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in the art; for example, see: Remington's Pharmaceutical Sciences, Mack Publishing Company, Easton, Pa., 16th Edition, 1980. The composition of the formulation to be administered will, in any event, contain a quantity of the active adenosine agent in an amount effective for treatment.

Parenteral administration is generally characterized by injection, either subcutaneously, intramuscularly or intravenously. Injectables can be prepared in conventional forms, either as liquid solutions or suspension, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of active adenosine antagonist or agonist administered will, of course, be dependent on the subject being treated, the severity and nature of the affliction, the manner of administration, the potency and pharmacodynamics of the particular agent and the judgement of the prescribing physician. However, the therapeutically effective dosage for use in this invention will generally be in the range from about 0.01 mu g/kg (body weight) to 5 mg/kg.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrastemal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracistemally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

In another aspect, the present invention provides pharmaceutically acceptable compositions which comprise a therapeutically-effective amount of one or more of the subject co,pounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intravectally, for example, as a pessary, cream or foam.

The compounds according to the invention may be formulated for administration in any convenient way for use in human or veterinary medicine, by analogy with other pharmaceuticals.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Oreg., U.S.A., 1977).

Combinatorial Libraries

In the current era of drug development, high throughput screening of thousands to millions of compounds plays a key role. High throughput screening generally incorporates automation and robotics to enable testing these thousands to millions of compounds in one or more bioassays in a relatively short period of time. This high capacity screening technique requires enormous amounts of "raw materials" having immense molecular diversity to fill available capacity. Accordingly, combinatorial chemistry will play a significant role in meeting this demand for new molecules for screening. Once "leads" are identified using high throughput screening techniques, combinatorial chemistry will be advantageously used to optimize these initial leads (which analogs/variants will be tested in the same high throughput screening assay(s) that identified the initial lead).

A combinatorial library for the purposes of the present invention is a mixture of chemically-related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) *Trends Anal. Chem.* 14:83; the Affymax U.S. Pat. Nos. 5,359,115 and 5,362,899; the Ellman U.S. Pat. No. 5,288,514: the Still et al. PCT publication WO 94/08051; Chen et al. (1994) *JACS* 116:2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologes are provided below.

A) Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

D) Multipin Synthesis

The libraries of the subject method can take the multipin library format. Briefly, Geysen and co-workers (Geysen et al. (1984) *PNAS* 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) *Tetrahedron Lett* 31:5811–5814; Valerio et al. (1991) *Anal Biochem* 197:168–177; Bray et al. (1991) *Tetrahedron Lett* 32:6163–6166).

C) Divide-Couple-Recombine

In yet another embodiment, a variegated library of compounds can be provided on a set of beads utilizing the strategy of divide-couple-recombine (see, e.g., Houghten (1985) *PNAS* 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) *PNAS* 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271–280; Fodor, S. P. A. (1991) *Science* 251:767; Pirrung et al. (1992) U.S. Pat. No. 5,143,854; Jacobs et al. (1994) *Trends Biotechnol* 12:19–26). The spatial resolution of photolithography affords miniaturization. This technique can be carried out through the use protection/deprotection reactions with photolabile protecting groups.

The key points of this technology are illustrated in Gallop et al. (1994) *J Med Chem* 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with sequenceable bio-oligomers

The principle of using oligonucleotides to encode combinatorial synthetic libraries was described in 1992 (Brenner et al. (1992) PNAS 89:5381–5383), and an example of such a library appeared the following year (Needles et al. (1993) *PNAS* 90:10700–10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In certain embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) *J Am Chem Soc* 115:2529–2531), orthogonality in synthesis is achieved by employing acid-labile protection for the coding strand and base-labile protection for the compound strand.

In an alternative approach (Nikolaiev et al. (1993) *Pept Res* 6:161–170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) *Tetrahedron Lett* 32:3891–3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-sequenceable Tagging: Binary Encoding

An alternative form of encoding the test compound library employs a set of non-sequencable electrophoric tagging molecules that are used as a binary code (Ohlmeyer et al. (1993) *PNAS* 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 10% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Org Chem* 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027–6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

Exemplification

The invention now being generally described, it will be more readily understood by reference to the following examples, which are included merely for purposes of illustration of certain aspects and embodiments of the present invention, and are not intended to limit the invention.
General Methods Utilized in the Examples NMR spectra were acquired at proton frequencies of 270 and 300 MHz, using $CDCl_3$ as solvent unless noted otherwise. $^1H$ chemical shifts are reported relative to $Me_4Si$ ("TMS"; δ=0.00 ppm) or $CHCl_3$ (δ=7.26 ppm) as internal standards; $^{31}P$ chemical shifts are relative to external aqueous 85% $H_3PO_4$ (δ=0.00 ppm); and $^{13}C$ chemical shifts are relative to $CHCl_3$ (δ=77.00 ppm) or TMS (δ=0.00 ppm) as internal standards. Mass spectra were obtained in electron impact ionization mode at 70 eV. Optical rotations were measured at rt.

EXAMPLE 1
Synthesis of Racemic Diester 2

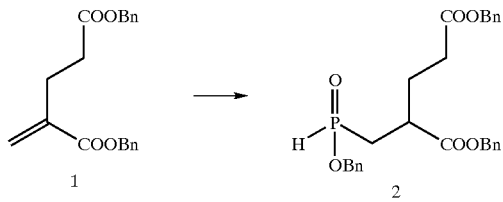

Anhydrous sodium hypophosphite (prepared from sodium hypophosphite monohydrate by azeotropic distillation with toluene in vacuo at 50° C.) (940 mg, 10.8 mmol) was suspended in 60 mL of dry $CH_2Cl_2$ and cooled to 0° C., then triethylamine (2.50 mL, 18.9 mmol) and chlorotrimethylsilane (2.32 mL, 18.4 mmol) were added. After 5 min, compound 1 (500 mg, 1.54 mmol) in 5 mL of dry $CH_2Cl_2$ was added. The mixture was stirred at rt for 24 h before 1 N HCl (20 mL) was added. The reaction mixture was extracted with $CH_2Cl_2$ (3×40 mL), and the combined organic phases were dried ($MgSO_4$). After concentration, the residue was dissolved in 6 mL of dry $CH_2Cl_2$ and 0.6 mL of pyridine and cooled to 0° C., then trimethylacetyl chloride (0.3 mL, 2.25 mmol) was added followed by benzyl alcohol (0.21 mL, 1.8 mmol). The mixture was stirred at 0° C. to rt for 2 h, then diluted with ether. The organic layer was washed with 1 N HCl (10 mL), $H_2O$ (10 mL), and brine (10 mL), dried ($MgSO_4$), and concentrated. Flash chromatography over silica gel with $CHCl_3$—MeOH (30:1) as eluent gave racemic compound 2 (657 mg, 89%) as a colorless oil: $^1H$ NMR ($CDCl_3$, 300 MHz) δ7.22 (d, $J_{H,P}$=555 Hz, 0.6H), 7.19 (d, $J_{H,P}$=550 Hz, 0.4H), 7.39–7.34 (m, 15H), 5.15–4.95 (m, 6H), 2.98 (m, 1H), 2.47–2.17 (m, 3H), 2.14–1.79 (m, 3H); $^{31}P$ NMR ($CDCl_3$, 121 MHz) δ36.06, 35.08; $^{13}C$ NMR ($CDCl_3$, 75 MHz) δ173.46, 173.39, 172.13, 135.70, 135.30, 128.73, 128.60, 128.58, 128.53, 128.46, 128.43, 128.38, 128.33, 128.26, 128.20, 67.88, 67.79, 67.07, 66.99, 66.46, 38.05, 38.02, 31.25, 30.02, 28.29, 28.13.

EXAMPLE 2

Synthesis of Racemic Tetraester 3

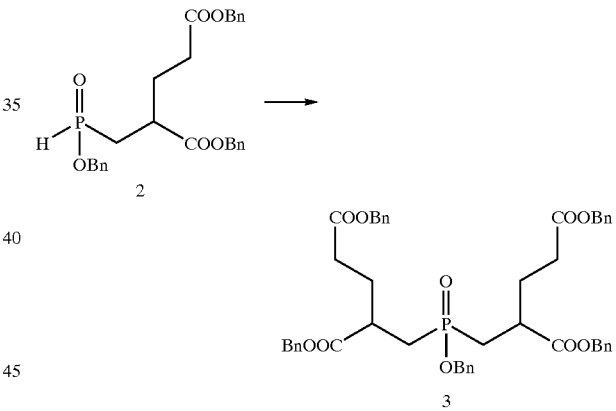

To a solution of 2 (210 mg, 0.44 mmol) in 5 mL of dry THF was added sodium hydride (15 mg, 60% dispersion in oil, 0.44 mmol) followed by compound 1 (140 mg, 0.44 mmol) at 0° C., and the mixture was stirred at rt for 2 h before 1 N HCl was added. The reaction mixture was extracted with $CH_2Cl_2$ (3×20 mL). The combined organic layers were dried ($MgSO_4$) and concentrated. Flash chromatography over silica gel with ethyl acetate-hexanes (1:1) as eluent gave compound 3 (45 mg, 13%) as a colorless oil: $^1H$ NMR ($CDCl_3$, 300 MHz) δ7.34–7.27 (m, 25H), 5.06–4.89 (m, 10H), 2.83 (m, 2H), 2.33–2.14 (m, 6H), 2.00–1.60 (m, 6H); $^{31}P$ NMR ($CDCl_3$, 121 MHz) δ–28.51, –28.90 –29.34, $^{13}C$ NMR ($CDCl_3$, 75 MHz) δ173.80, 172.19, 136.27, 135.79, 135.50, 128.60, 128.56, 128.42, 128.33, 128.28, 128.24, 128.19, 128.14, 66.91, 66.87, 66.80, 66.37, 66.10, 66.02, 38.65, 38.51, 31.71, 30.32, 31.24, 30.67, 30.57, 30.04, 28.85, 28.69.

EXAMPLE 3
Synthesis of Racemic Tetraacid FN-6

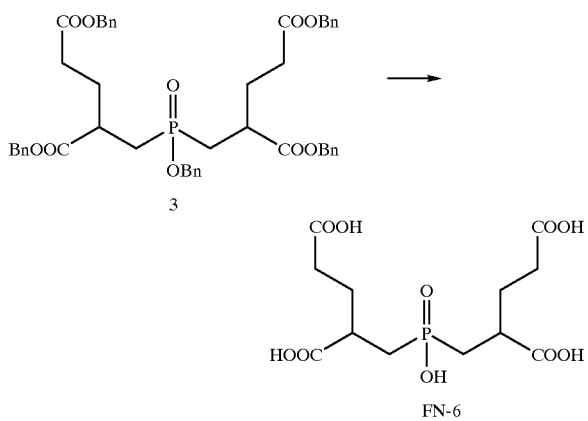

To a solution of 3 (42 mg, 0.52 mmol) in tert-butanol was added 30 mg of 20% Pd(OH)$_2$/C (Aldrich, ≦50% H$_2$O), and the mixture was hydrogenated under 70 psi of H$_2$ for 24 h. The catalyst was removed by filtration through celite, and the filtrate was concentrated. The residue was dissolved in 5 mL of water and lyophilized to afford 17 mg (92%) of FN-6 as a white solid: $^1$H NMR (D$_2$O, 300 MHz) δ2.77 (m, 2H), 2.44 (t, J=7.3 Hz, 4H), 2.20 (dt, J=13.2, 11.3 Hz, 2H), 2.00–1.82 (m, 6H); $^{31}$P NMR (D$_2$O 121 MHz) δ–33.12; $^{13}$C NMR (D$_2$O, 75 MHz) δ179.69, 179.61, 178.61, 39.89, 32.70, 32.28, 31.49, 29.68, 29.58, 29.52, 29.42.

EXAMPLE 4
Synthesis of Diester 5

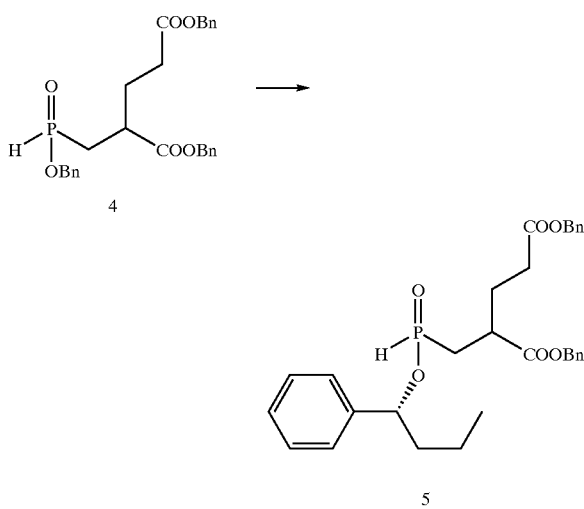

Compound 4 (130 mg, 0.33 mmol) was dissolved in 2 mL of dry CH$_2$Cl$_2$ and 0.2 mL of pyridine and cooled to 0° C., then trimethylacetyl chloride (80 μL, 0.6 mmol) was added followed by (R)-(+)-1-phenyl-1-butanol (65 mg, 0.44 mmol). The mixture was stirred at 0° C. to rt for 2 h, then diluted with ether, and the reaction mixture was washed with 1N HCl (10 mL), H$_2$O (10 mL), and brine (10 mL), dried (MgSO$_4$), and concentrated. Flash chromatography over silica gel with CHCl$_3$—MeOH (30:1) as eluent gave 5 (164 mg, 94%) as a mixture of four diastereoisomers. $^1$H NMR (CDCl$_3$, 300 MHz) δ7.45–7.28 (m, 15H), 7.26 (d, J$_{H,P}$=558 Hz, 0.24H), 7.23 (d, J$_{H,P}$=554 Hz, 0.16H), 6.91 (d, J$_{H,P}$=552 Hz, 0.60H), 5.37–5.24 (m, 1H), 5.17–5.03 (m, 4H), 3.05–2.68 (m, 1H), 2.56–1.60 (m, 8H), 1.50–1.20 (m, 2H), 0.98–0.91 (m, 3H); $^{31}$P NMR (CDCl$_3$, 121MHz) δ34.88, 34.10, 32.22, 31.32.

EXAMPLE 5
Synthesis of Tetraesters 6

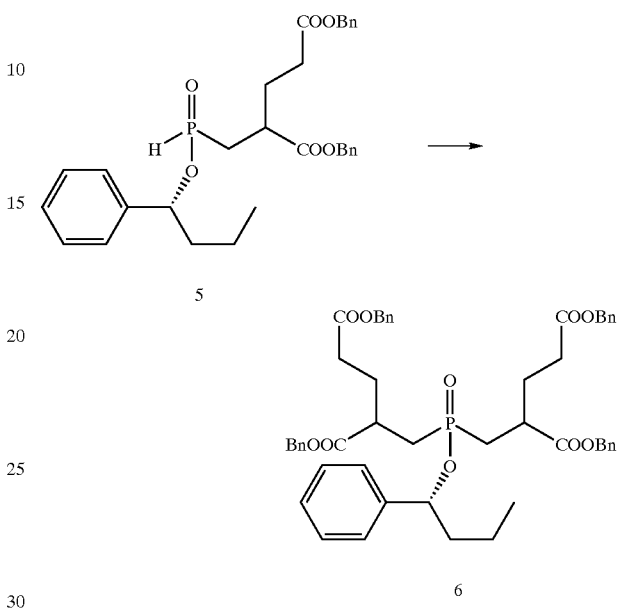

To a solution of 5 (220 mg, 0.44 mmol) in 5 mL of dry THF was added sodium hydride (15 mg, 60% dispersion in oil, 0.44 mmol) followed by compound 1 (See Example 1; 140 mg, 0.44 mmol) at 0° C., and the mixture was stirred at rt for 2 h. 1N HCl was added, and the mixture was extracted with CH$_2$Cl$_2$ (3×20 mL). The combined organic phases were dried (MgSO$_4$) and concentrated. Flash chromatography over silica gel with CHCl$_3$—MeOH (30:1) as eluent gave a mixture of four isomers (110 mg, 27%). $^{31}$P NMR showed four peaks: 67 –29.91, –30.21, –30.37, and –30.66. Careful preparative TLC separation (ethyl aceate-hexanes 2:3) gave homogeneous compounds 6a–d.

6a: R$_f$ 0.60 (ethyl acetate-hexanes 1:1); [α]$_D$+12.1° (c 0.7, CHCl$_3$); $^1$H NMR (CDCl$_3$, 300 MHz) δ7.37–7.28 (m, 25H) 5.30 (dt, J=8.7, 7.2 Hz, 1H), 5.20–4.97 (m, 8H), 2.91 (m, 1H), 2.56 (m, 1H), 2.39–2.22 (m, 3H), 2.10–1.60 (m, 11H), 1.35–1.09 (m, 2H), 0.87 (t, J=7.2 Hz, 3H); $^{31}$P NMR (CDCl$_3$, 121 MHz) δ–29.90; $^{13}$C NMR (CDCl$_3$, 75 MHz) δ173.93, 173.86, 173.78, 173.70, 172.23, 172.12, 140.98, 135.78, 135.55, 128.59, 128.51, 128.46, 128.25, 128.23, 128.17, 126.55, 77.19, 77.10, 66.82, 66.76, 66.31, 66.23, 40.45, 40.38, 38.67, 38.63, 38.59, 38.56, 32.18, 31.30, 31.09, 30.93, 30.11, 29.66, 28.84, 28.69, 28.64, 28.48, 18.58, 13.68.

6b: R$_f$ 0.58 (ethyl acetate-hexanes 1:1); [α]$_D$+12.9° (c 0.35, CHCl$_3$); $^1$H NMR (CDCl$_3$, 300 MHz) δ7.37–7.28 (m, 25H), 5.30 (dt, J=9.0, 6.6 Hz, 1H), 5.21–4.99 (m, 8H), 2.99 (m, 1H), 2.55 (m, 1H), 2.41–2.20 (m, 3H), 2.10–1.62 (m, 11H), 1.40–1.20 (m, 2H), 0.86 (t, J=7.2 Hz, 3H); $^{31}$P NMR (CDCl$_3$, 121 MHz) δ–30.32; $^{13}$C NMR (CDCl$_3$, 75 MHz) δ173.94, 173.90, 173.87, 173.81, 172.25, 172.15, 141.01, 135.82, 135.58, 135.52, 128.62, 128.57, 128.54, 128.49, 128.32, 128.28, 128.26, 128.24, 128.22, 128.21, 128,19, 126.58, 77.20, 77.16, 66.82, 66.79, 66.33, 66.25, 40.44, 40.37, 38.70, 38.67, 38.43, 38.38, 32.25, 31.90, 31.34, 31.13, 31.00, 30.75, 29.70, 28.81, 28.67, 28.53, 28.38, 18.55, 13.71.

6c: $R_f$ 0.57 (ethyl acetate-hexanes 1:1); $[\alpha]_D$ 0° (c 0.42, CHCl$_3$); $^1$H NMR (CDCl$_3$, 300 MHz) δ7.35–7.20 (m, 25H), 5.29 (dt, J=9.3, 6.9 Hz, 1H), 5.17–4.94 (m, 8H), 2.91 (m, 1H), 2.45–2.25 (m, 3H), 2.20–1.20 (m, 14H), 0.84 (t, J=7.5 Hz, 3H); $^{31}$P NMR (CDCl$_3$, 121 MHz) δ–30.11; $^{13}$C NMR (CDCl$_3$, 75 MHz) δ173.84, 173.74, 173.70, 173.62, 172.25, 172.10, 140.84, 135.90, 131.60, 135.49, 128.62, 128.53, 128.41, 128.32, 128.24, 128.21, 126.68, 77.24, 77.15, 66.87, 66.79, 66.33, 66.25, 40.27, 40.21, 38.86, 38.83, 38.46, 38.41, 31.95, 31.62, 31.30, 31.19, 30.80, 30.39, 29.70, 28.64, 28.53, 28.48, 28.40, 18.63, 13.73.

6d: $R_f$ 0.55 (ethyl acetate-hexanes 1:1); $[\alpha]_D$ –2.8° (c 0.42, CHCl$_3$); $^1$H NMR (CDCl$_3$, 300 MHz) δ7.41–7.20 (m, 25H), 5.31 (dt, J=9.3, 6.9 Hz, 1H), 5.23–4.98 (m, 8H), 2.97 (m, 1H), 2.50–2.17 (m, 4H), 2.15–1.82 (m, 6H), 1.80–1.50 (m, 5H), 1.45–1.20 (m, 2H), 0.85 (t, J=7.2 Hz, 3H); $^{31}$P NMR (CDCl$_3$, 121 MHz) δ–30.57; $^{13}$C NMR (CDCl$_3$, 75 MHz) δ173.77, 173.70, 173.66, 173.59, 172.18, 172.06, 140.81, 135.77, 135.50, 135.46, 128.59, 128.53, 128.51, 128.41, 128.30, 128.23, 128.19, 126.58, 77.16, 77.05, 66.82, 66.31, 66.24, 40.29, 40.23, 38.79, 38.30, 38.24, 31.96, 31.44, 31.34, 31.14, 30.81, 30.20, 28.95, 28.80, 28.69, 28.53, 18.54, 13.69.

EXAMPLE 6
Synthesis of Optically-Pure Stereoisomers of Tetracid FN-6

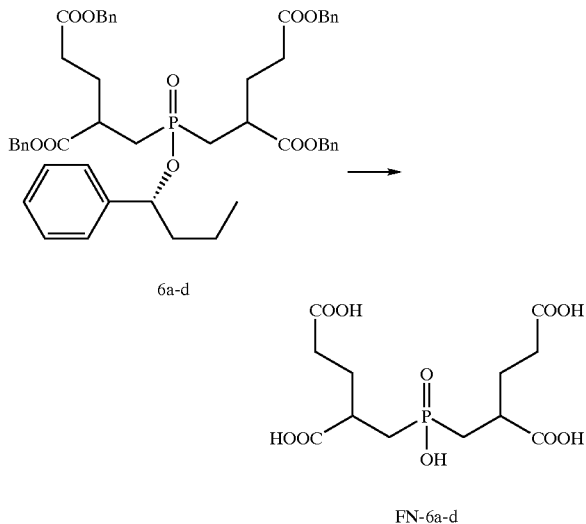

6a-d

FN-6a-d

The synthetic procedure outlined for the preparation of FN-6 (See Example 3) was utilized for the preparation of optically-pure stereoisomers FN-6a–d.

FN-6a (yield 94%): white solid; $^1$H NMR (D$_2$O, 300 MHz) δ2.76 (m, 2H), 2.45 (t, J=7.5 Hz, 4H), 2.14 (dt, J=12.9, 9.6 Hz, 2H), 2.00–1.89 (m, 4H), 1.83 (dt, J=14.4, 4.2 Hz, 2H); $^{31}$P NMR (D$_2$O, 121 MHz) δ–37.63; $^{13}$C NMR (D$_2$O, 75 MHz) δ179.95, 178.74, 40.16, 32.55 (d, $J_{1,P}$=90.23 Hz), 32.38, 29.67 (d, $J_{3,P}$=11.48 Hz).

FN-6b (yield 96%): white solid; $^1$H NMR (D$_2$O, 300 MHz) δ2.76 (m, 2H), 2.45 (t, J=7.8 Hz, 4H), 2.13 (dt, J=12.6, 10.5 Hz, 2H), 2.04–1.89 (m, 4H), 1.83 (dt, J=15.0 4.2 Hz, 2H); $^{31}$P NMR (D$_2$O, 121 MHz) δ–36.42; $^{13}$C NMR (D$_2$O, 75 MHz) δ180.07, 178.76, 40.10, 32.67 (d, $J_{1,P}$=90.75 Hz), 32.40, 29.57 (d, $J_{3,P}$=11.25 Hz).

FN-6c (yield 99%): white solid; $^1$H NMR (D$_2$O, 300 MHz) δ2.76 (m, 2H), 2.45 (t, J=7.5 Hz, 4H), 2.09 (dt, J=12.6, 9.0 Hz, 2H), 2.04–1.88 (m, 4H), 1.79 (dt, J=15.0 4.2 Hz, 2H); $^{31}$P NMR (D$_2$O, 121 MHz) δ–37.96; $^{13}$C NMR (D$_2$O, 75 MHz) δ179.88, 178.72, 40.13, 32.46 (d, $J_{1,P}$=90.75 Hz), 32.36, 29.66 (d, $J_{3,P}$=12 Hz).

FN-6d (yield 96%); white solid; $^1$H NMR (D$_{20}$, 300 MHz) δ2.76 (m, 2H), 2.45 (t, J=7.5 Hz, 4H), 2.14 (dt, J=13.2, 9.6 Hz, 2H), 2.00–1.86 (m, 4H), 1.85 (dt, J=14.7 3.6 Hz, 2H); $^{31}$P NMR (D$_2$O, 121 MHz) δ–35.56; $^{13}$C NMR (D$_2$O, 75 MHz) δ179.88, 178.72, 40.13, 32.46 (d, $J_{1,P}$=90.75 Hz), 32.37, 29.66 (d, $J_{3,P}$=12 Hz).

EXAMPLE 7

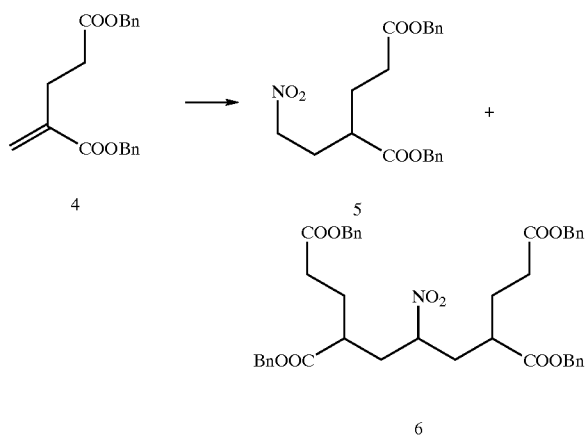

To a solution of 4 (400 mg, 1.23 mmol) in nitromethane was added 0.1 mL of Triton B (40% solution in methanol). The mixture was stirred at room temperature for 5 h. The nitromethane was removed under reduced pressure. Flash chromatography over silica gel with ethyl acetate-hexanes (8:1 to 3:1) as eluent gave compounds 5 (200 mg, 42%) and 6 (150 mg, 17%) as colorless oil. 5: IR (film) υ1730 cm$^{-1}$, $^1$H NMR (CDCl$_3$, 300 MHz) δ7.40–7.28 (m, 10H), 5.13 (s, 2H), 5.10 (s, 2H), 4.35 (m, 2H), 2.45–2.15 (m, 4H), 2.08–1.82 (m, 2H); $^{13}$C NMR(CDCl$_3$, 75 MHz) δ173.52, 172.22, 135.67, 135.32, 128.66, 128.57, 128.51, 128.32, 128.28, 73.01, 66.89, 66.48, 41.40, 31.41, 28.95, 26.94. 6: IR (film) υ1731 cm$^{-1}$ $^1$H NMR (CDCl$_3$, 300 MHz) δ7.39–7.20 (m, 20H), 5.15–5.02 (m, 8H), 4.53 (m, 1H), 2.52–2.22 (m, 6H), 2.08–1.75 (m, 8H); $^{13}$C NMR (CDCl$_3$, 75 MHz) δ173.34, 172.10, 135.70, 135.37, 128.57, 128.40, 128.29, 128.27, 84.35, 66.87, 66.44, 41.17, 41.06, 35.83, 35.62, 31.32, 27.55, 27.41.

EXAMPLE 8

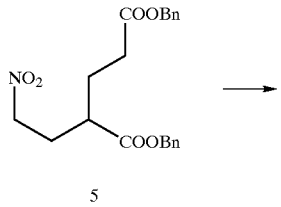

5

-continued

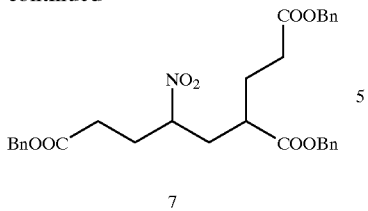

7

To a solution of compound 5 (58 mg, 0.15 mmol) and benzyl acrylate (25 mg, 0.15mmol) in 1 mL of dry $CH_2Cl_2$ was added a catalytic amount of Triton B (40% solution in methanol). The mixture was stirred at room temperature for 4 h. The solvent was removed under reduced pressure and flash chromatography over silica gel with ethyl acetate-hexanes (5:1) as eluent gave compound 7 (75 mg, 91%). $^1$H NMR (CDCl$_3$, 300 MHz) δ7.40–7.25 (m, 15H), 5.20–5.03 (m, 6H), 4.64–4.46 (m, 1H), 2.55–1.80 (m, 11H); $^{13}$C NMR (CDCl$_3$, 75 MHz) δ173.63, 172.10, 171.34, 135.67, 135.49, 128.60, 128.55, 128.41, 128.31, 128.27, 85.67, 85.03, 66.86, 66.67, 66.44, 41.17, 35.41, 35.32, 31.35, 30.07, 29.96, 29.07, 28.36, 27.48, 26.64.

EXAMPLE 9

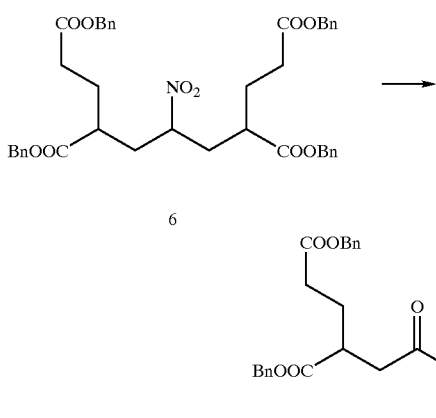

To a solution of compound 8 (54 mg, 0.076 mmol) in 2 mL of dry $CH_2Cl_2$ was added 18 uL of triethylamine, after being stirred at room temperature for 10 min, 80 mg of CATP was added. The resulting mixture was stirred for additional 4 h. Then 10 mL of ether was added and filtered through celite, and washed with ether. The filtrate was concentrated. Chromatography afforded 8 (30 mg, 58%): $^1$H NMR (CDCl$_3$, 300 MHz) δ7.40–7.22 (m, 20H), 5.15–5.01 (m, 8H), 3.00–2.79 (m, 4H), 2.50–2.30 (m, 6H), 2.00–1.78 (m, 4H); $^{13}$C NMR (CDCl$_3$, 75 MHz) δ205.98, 205.73, 174.20, 174.03, 172.45, 172.40, 135.78, 135.68, 128.53, 128.51, 128.22, 128.16, 66.58, 66.33, 43.95, 39.27, 31.62, 31.59, 29.68, 26.66, 26.59.

EXAMPLE 10

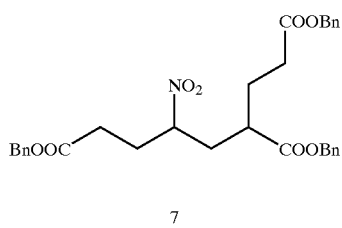

7

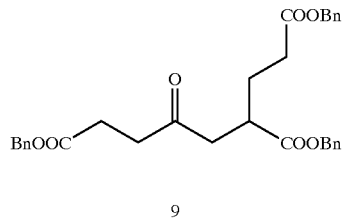

9

To a solution of compound 7 (70 mg, 0.13 mmol) in 5 mL of dry $CH_2Cl_2$ was added 30 uL of triethylamine, after being stirred at room temperature for 10 min, 120 mg of CATP was added. The resulting mixture was stirred for an additional 4 h, then 20 mL of ether was added and filtered through celite, and washed with ether. The filtrate was concentrated. Chromatography afforded 9 (40 mg, 60%). $^1$H NMR (CDCl$_3$, 300 MHz) δ7.40–7.25 (m, 15H), 5.16–5.05 (m, 6H), 3.02–2.90 (m, 2H), 2.80–2.50 (m, 5H), 2.36 (t, J=7.2 Hz, 2H), 2.00–1.89 (m, 2H); $^{13}$C NMR (CDCl$_3$, 75 MHz) δ206.30, 174.20, 172.43, 172.36, 135.76, 135.70, 128.51, 128.49, 128.20, 128.17, 128.15, 66.57, 66.47, 66.33, 43.92, 39.33, 37.06, 31.62, 27.85, 26.65.

EXAMPLE 11

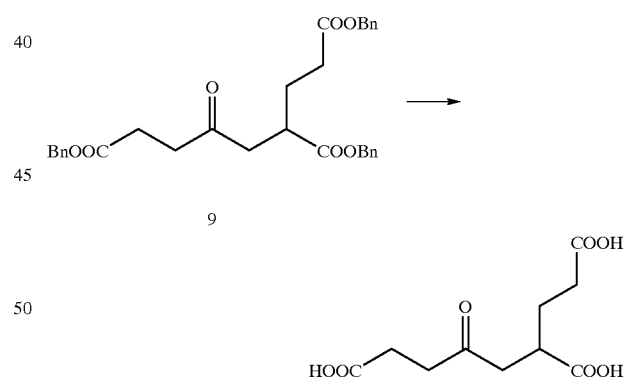

To a solution of 9 (40 mg, 0.078 mmol) in tert-butanol was added 30 mg of 20% Pd(OH)$_2$/C (Aldrich, ≦50% H$_2$O), and the mixture was hydrogenated under 1 atm of H$_2$ for 4 h. The catalyst was removed by filtration through celite, and the filtrate was concentrated. The residue was dissolved in 5 mL of water and lyophilized to afford 18 mg (94%) of 1 as a syrup. 1: $^1$H NMR (CDCl$_3$, 300 MHz) δ3.03–2.74 (m, 5H), 2.59 (t, J=6.0 Hz, 2H), 2.44 (t, J=7.2 Hz, 2H), 1.96–1.76 (m, 2H).

EXAMPLE 12

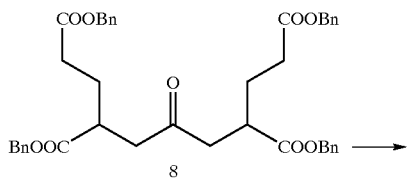

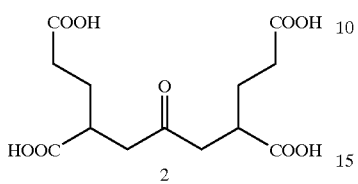

To a solution of 8 (24 mg, 0.034 mmol) in tert-butanol was added 10 mg of 20% Pd(OH)$_2$/C (Aldrich, ≦50% H$_2$O), and the mixture was hydrogenated under 1 atm of H$_2$ for 4 h. The catalyst was removed by filtration through celite, and the filtrate was concentrated. The residue was dissolved in 5 mL of water and lyophilized to afford 10 mg (93%) of 2 as a syrup. 2: $^1$H NMR (CDCl$_3$, 300 MHz) δ3.03–2.72 (m, 6H), 2.45 (t, J=7.5 Hz, 4H), 1.96–1.75 (m, 4H).

EXAMPLE 13

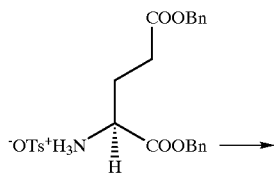

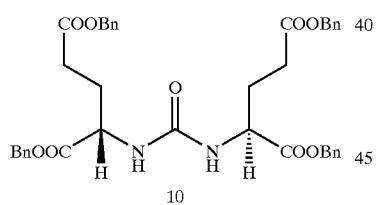

To a suspension of dibenzyl L-glutamate tosylate (1 g, 2mmol) in 20 mL of CH$_2$Cl$_2$ was added triphosgene (110 mg, 0.37 mmol). The mixture was cooled to −78° C., and Et$_3$N (0.53 mL, 4 mmol) was added. The reaction mixture was allowed to warm to room temperature and stirred for an additional 2 h. The reaction mixture was diluted with 100 mL of EtOAc and washed with H$_2$O (3×30 mL), brine (30 mL) and dried over MgSO$_4$. The solvent was evaporated and the residue was dissolved in 5 mL of CH$_2$Cl$_2$, and excess hexane was added. The white solid 10 was collected (600 mg, 88%). $^1$H NMR (CDCl$_3$, 300 MHz) δ7.40–7.25 (m, 20H), 5.17 (br s, 2H), 5.13 (br s, 4H), 5.08 (s, 4H), 4.53 (dt, J=8.1, 4.8 Hz, 2H), 2.41 (m, 4H), 2.19 (m, 2H), 1.97 (m, 2H); $^{13}$C NMR (CDCl$_3$, 75 MHz) δ172.70, 172.51, 156.53, 135.67, 135.12, 128.51, 128.46, 128.33, 128.14, 67.18, 66.38, 52.47, 30.17, 27.84.

EXAMPLE 14

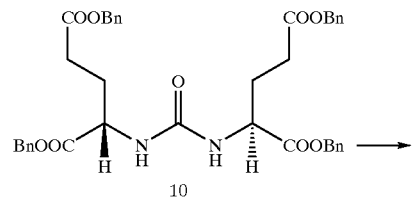

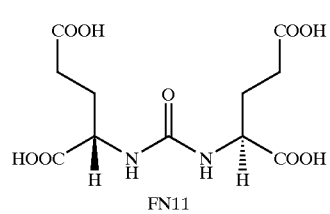

To a solution of 10 (510 mg, 0.75 mmol) in tert-butanol was added 200 mg of 20% Pd(OH)$_2$/C (Aldrich, ≦50% H$_2$O), and the mixture was hydrogenated under 1 atm of H$_2$ for 24 h. The catalyst was removed by filtration through celite, and the filtrate was concentrated. The residue was dissolved in 15 mL of water and lyophilized to afford 235 mg (98%) of FN11 as a white solid: [α]$_D$ −16.4° (c 0.5, H2O); $^1$H NMR (D$_2$O, 300 δ4.26 (br s, 2H), 2.51 (t, J=9.9 Hz, 4H), 2.18 (m, 2H), 1.98 (m, 2H); $^{13}$C NMR (D$_2$O, 75 MHz) δ178.59, 177.59, 160.55, 53.91, 31.36, 27.51.

EXAMPLE 15

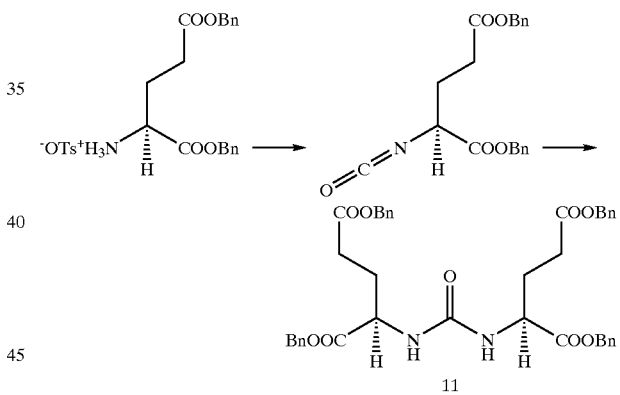

To a suspension of dibenzyl L-glutamate tosylate (1 g, 2 mmol) in 20 mL of CH$_2$Cl$_2$ was added triphosgene (200 mg, 0.66 mmol). The mixture was cooled to −78° C., then Et$_3$N (0.60 mL, 4 mmol) was added. The reaction mixture was stirred at −78° C. for 2 h, then allowed to warm to room temperature and diluted with 100 mL of EtOAc and washed with H$_2$O (30 mL), 1N HCl (30 mL) and brine (30 mL). The mixture was dried over MgSO$_4$. The solvent was evaporated and the residue was chromatographed on silica gel with hexanes/EtOAc (2:1) to give isocyanate (230 mg). The isocyanate (230 mg, 0.65 mmol) was dissolved in 5 mL of CH$_2$Cl$_2$, and dibenzyl L-glutamate (213 mg, 0.65 mmol) was added at 0° C. The mixture was stirred at room temperature for 24 h. Excess hexane was added. The white solid 11 was collected (440 mg, 99% from isocyanate). $^1$H NMR (CDCl$_3$, 300 MHz) δ7.35–7.25 (m, 20H), 5.51 (d, J=7.8 Hz, 2H), 5.11 (s, 4H), 5.06 (s, 4H), 4.52 (dt, J=7.8, 5.4 Hz, 2H), 2.41 (m, 4H), 2.19 (m, 2H), 1.98 (m, 2H); $^{13}$C NMR (CDCl$_3$, 75 MHz) δ172.79, 172.68, 156.78, 135.75, 135.21, 128.57, 128.53, 128.38, 128.23, 128.19, 67.22, 66.42, 52.53, 30.25, 27.88.

EXAMPLE 16

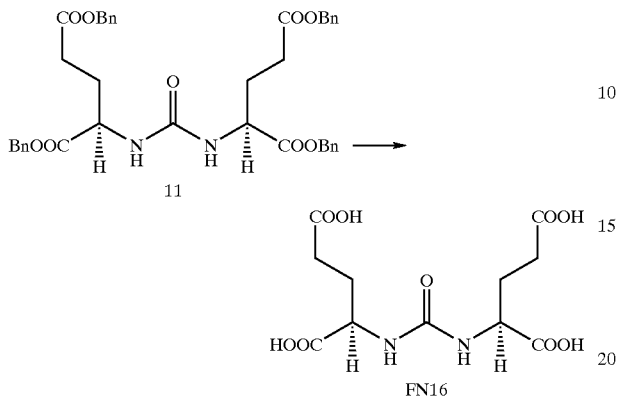

The general procedure outlined in Example 14 was followed for the preparation of FN16 from 11. FN16: $^1$H NMR (D$_2$O, 300 MHz) δ4.24 (m, 2H), 2.45 (t, J=7.2 Hz, 4H), 2.15 (m, 2H), 1.95 (m, 2H); $^{13}$C NMR (D$_2$O, 75 MHz) δ178.48, 177.40, 160.34, 53.80, 31.34, 27.62.

EXAMPLE 17

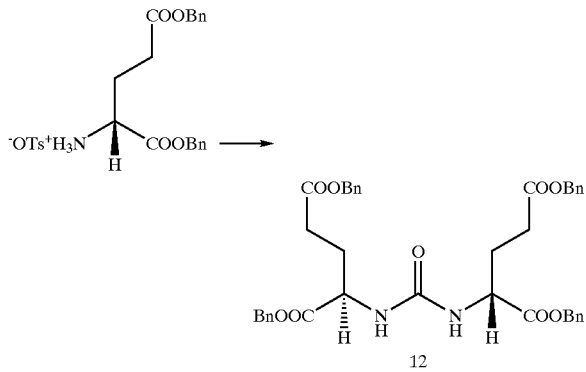

The general procedure outlined in Example 13 was followed for the preparation of 12 from dibenzyl D-glutamate tosylate.

EXAMPLE 18

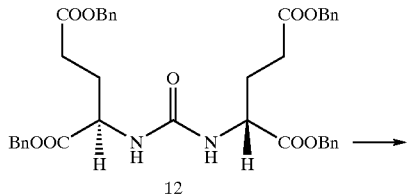

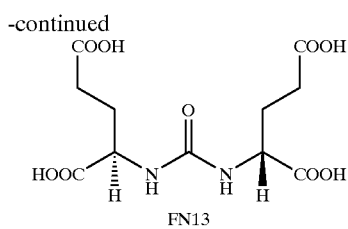

The general procedure outlined in Example 14 was followed for the preparation of FN13 from 12. FN13: $[\alpha]_D$+ 17.1° (c 0.84, H$_2$O); $^1$H NMR (D$_2$O, 300 MHz) and $^{13}$C NMR (D$_2$O, 75 MHz) were same as for FN11.

EXAMPLE 19

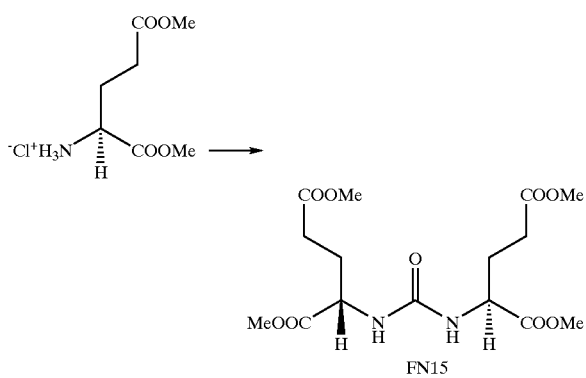

To a suspension of dimethyl L-glutamate chloride (2.1 g, 10 mmol) in 40 mL of CH$_2$Cl$_2$ was added triphosgene (1 g, 3.3 mmol). The mixture was cooled to −78° C., then Et$_3$N (3 mL, 20 mmol) was added. The reaction mixture was stirred at −78° C. for 0.5 h, then allowed to warm to room temperature and diluted with 100 mL of EtOAc and washed with H$_2$O (30 mL), 1N HCl (30 mL) and brine (30 mL). The mixture was dried over MgSO$_4$. The solvent was evaporated and the residue was chromatographed on silica gel with hexanes/EtOAc (2:1) to give the corresponding isocyanate (870 mg). The isocyanate (870 mg, 4.3 mmol) was dissolved in 10 mL of CH$_2$Cl$_2$, and dimethyl L-glutamate (752 mg, 4.3 mmol) was added at 0° C. The mixture was then stirred at room temperature for 24 h. Excess hexane was added, and the white solid FN15 was collected (1.50 g, 92% from isocyanate). $^1$H NMR (CDCl$_3$, 300 MHz) δ5.47 (d, J=7.8 Hz, 2H), 4.50 (dt, J=8.1, 5.1 Hz, 2H), 3.75 (s, 6H), 3.67 (s, 6H), 2.42 (m, 4H), 2.17 (m, 2H), 1.96 (m, 2H); $^{13}$C NMR (CDCl$_3$, 75 MHz) δ173.47, 173.36, 156.71, 52.45, 52.40, 51.79, 30.03, 27.92.

EXAMPLE 20

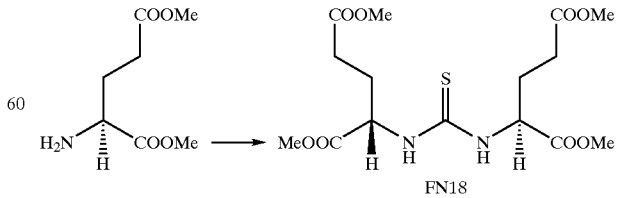

To a solution of dimethyl L-glutamate (575 mg, 3.28mmol) in 15 mL of CH$_2$Cl$_2$ was added thiophosgene (187 mg, 1.64 mmol). The mixture was cooled to −78° C., then Et$_3$N (0.43 mL, 3.28 mmol) was added. The reaction mixture was stirred at −78° C. for a short period, then allowed to warm to room temperature over 15 h. The mixture was then diluted with 100 mL of EtOAc and washed with H$_2$O (30 mL), 1N HCl (30 mL) and brine (30 mL). The mixture was dried over MgSO$_4$. The solvent was evaporated and the residue was chromatographed on silica gel with hexanes/EtOAc (3:1→1:1) to give FN18 (410 mg, 64%). $^1$H NMR (CDCl$_3$, 300 MHz) δ5.08 (d, J=7.8 Hz, 2H), 4.50 (m, 2H), 3.78 (s, 6H), 3.68 (s, 6H), 2.46 (m, 4H), 2.25 (m, 2H), 2.12 (m, 2H); $^{13}$C NMR (CDCl$_3$, 75 MHz) δ182.89, 173.47, 172.89, 56.19, 52.57, 51.82, 29.87, 27.40.

EXAMPLE 21
Antitumor Activity of FN11

Figure 15:
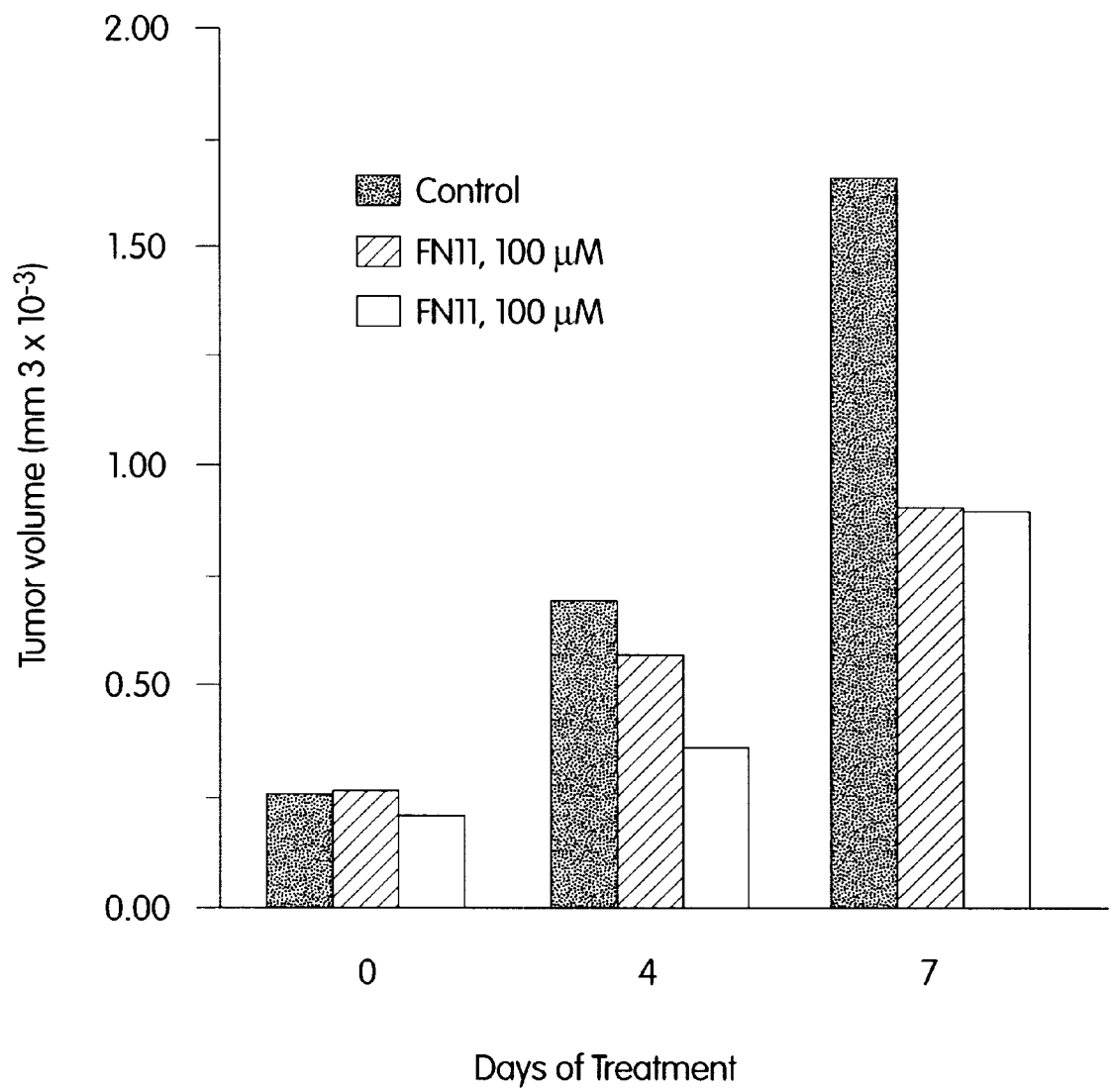
FIG. 15 presents a plot of tumor volume versus duration of treatment for glioblastoma xenografts treated with a compound of the present invention at 10 and 100 $\mu$M, contrasted with a control.

Implanted xenografts were formed by s.c. inoculation with 2×10$^6$ U-87 glioblastoma multiforme cells mixed with 0.5 mg Matrigel. FN11 was dissolved in PBS to a concentration of either 10 or 100 μM, and injections (0.1 mL) were made once daily into the base of the s.c. implanted xenografts. The starting volumes of the tumors were approximately 250 mm$^3$. The results from this protocol are depicted in FIG. 15.

EXAMPLE 22
Antiangiogenesis Activity of FN11

Control tumors and tumors grown under the conditions described in Example 21 were harvested at the end of 7 days, fixed in formalin and embedded in paraffin for sectioning. Tissue was stained immunohistochemically for von Willebrand's factor (vWF) to obtain a measure of vascularization. FIGS. 13 and 14 present the results of this protocol for the tumor treated with FN11 at 100 μM. FIG. 13 was taken at low magnification (100×), whereas FIG. 14 was taken at high magnification (400×). The Figures reveal a preponderance of avascular and low vascular areas, mostly small vessels, in the tumor treated with FN11 at 100 μM.

EXAMPLE 23
Studies of Neuroprotective Properties of FN Compounds

The testing of neuroprotective effects of ligands acting at metabotropic glutamate receptors requires the use of specific models that allow to visualize the action of these compounds. As it has been shown in several publications, protection against excitotoxicity (which may be induced by NMDA application) often requires the presence of glial cells, and cannot be demonstrated in cultures containing only neuronal cells. It is believed that the neuroprotective action of group II mGluR agonists result form an action at mGluR3 or mGluR2 receptors located on glial cells, which induces the release of neurotrophic factors from these glial cells.

We have tested the validity of these statements using three models of NMDA toxicity in cultures of cortical neurons prepared from fetal mice. The first model (A) consists of using a culture containing neurons without glial cells. NMDA (75 μM) is applied for 10 min without or with the tested compound. Then the culture medium is replaced and cells are left for 24 hours to develop toxicity. The second model (B) involves the use of mice cortical neurons which are seeded on a layer of confluent glial cells (mostly astrocytes) prepared from cerebral cortex of newborn mice. The incubations are identical as in model A. The third model (C) separates the neuronal and glial cultures. Glial cultures are treated with the tested neuroprotective compound in order to induce the release of protective factors into the medium. In parallel, cultures of cortical neurons (without glia) are treated for 10 min with NMDA (20 μM). Then NMDA is washed out and the neurons are treated with the medium collected from the treated glial cells. In all cases toxicity is assessed 24 hours after NMDA treatment by measurements of lactate dehydrogenase (LDH) activity accumulated in the medium during this period of time.

The comparison of the three models is shown in FIG. 16. As expected, in model A, ABHxD-I was not able to protect against NMDA toxicity. In contrast, when glial cells were present (model B) ABHxD-I produced a significant protection, reducing by over 40% the toxic effect of NMDA. This suggested that, in fact, ABHxD-I may induce the release of protective factors from glial cells. This possibility was tested in model C. As shown in FIG. 16, when incubated separately with glial cells, ABHxD-I was as effective as in model B. It should be noted that medium from untreated glial cells was not neuroprotective. This confirms the hypothesis that the action of ABHxD is mediated through the release of neuroprotective factors from glial cells. More importantly, this indicates that the neuroprotective effect of ABHxD-I does not depend on the presence of the drug during the toxic event, but the drug may be effective when added after the toxic stimulus.

The comparison of models B and C shows that both models reflect the indirect neuroprotective effect of ABHxD-I mediated through the action of the drug at receptors located on glial cells. This stresses the role of glial cells in mechanisms of brain injury and identifies these cells as a target of possible therapeutic intervention. From a practical point of view, for the purpose of testing compounds which act through this mechanism, model C appears superior to model B, as the variability of measurements is reduced in model C. This is reflected by a two-fold decrease in the standard error for the calculated means. This difference comes, most probably, from the nature of the LDH measurements. In model C, LDH can be only released from dying neurons and therefore it directly reflects the number of dead cells. In contrast, in model B, LDH levels may be affected by LDH leakage from glial cells. As the number of glial cells is large compared to neurons, even small leakage may result in significant changes in LDH levels. It is known that glial cells are not sensitive to NMDA toxicity, hence such increases do not reflect NMDA toxicity, but rather random variation which occurs in every living system. Hence, in model B, LDH release from dying neurons is measured on a higher background of variable control levels, which decreases the signal to noise ratio and increases the random variability of measurements. In our studies we initially used model B (as seen in FIGS. 17 and 18), but then switched to model C (FIGS. 19 and 20) which provided more reliable measurements.

Testing of FN Compounds

Initially, FN compounds were tested in model B. FIG. 17 shows the effects of FN1–FN8 used at 300 μM concentrations. Only FN1 and FN6 show about 30% of neuroprotection. Among FN6 enantiomers used at 100 μM concentrations (FIG.17), the 6/1 and 6/4 compounds appear more effective.

FN6 enantiomers were also tested in model C (FIG. 19). As in model B, the 6/1 and 6/4 compounds were more effective, the protection reaching about 30%. The Guilford compound PMPA, which is similar to FN6 was less effective. We also tested t several newer FN compounds in model C. As shown in FIG. 20, among those compounds only FN13 showed some neuroprotective effect which amounted to about 20% of protection.

Summary

The strongest effects—about 30%—are shown by FN1 and FN6. These effects are less than the neuroprotection seen with ABHxD-I, but better than the action of PMPA. The tested compounds may show greater efficacy in models of toxicity with a smaller necrotic component and a larger apoptotic component.

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A compound represented by generalized structure 1:

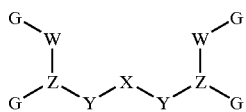

wherein

X is selected from the group consisting of —C(O)—, —C(S)—, —P(O)(N(R)$_2$)—, —P(NR)(OR)—, —P(NR)(N(R)$_2$)—, O, S, —S(O)—, —S(O)$_2$—, Se, —Se(O)—, —Se(O)$_2$—, —C(R)(OR)—, —C(R)(SR)—, —C(NR)—, —NR(O)—, and —N(OR)—;

Y is selected, independently for each occurrence, from the group consisting of (C(R)$_2$)$_n$, (NR)$_n$, (PR)$_n$, and a bond;

Z is selected, independently for each occurrence, from the group consisting of C(R), C(N(R)$_2$), C(NHacyl), N, and P;

W is selected, independently for each occurrence, from the group consisting of (C(R)$_2$)$_m$, (NR)$_m$, (PR)$_m$, and a bond;

G is selected, independently for each occurrence, from the group consisting of —COOH, —C(O)NHOH, —C(O)NH$_2$, —C(S)SH, —SO$_3$H, —SO$_2$H, —SOH, —SeO$_3$H, —SeO$_2$H, —SeOH, —S(O)$_2$NH$_2$, —P(O)(OH)$_2$, and —P(OH)$_2$;

R is selected, independently for each occurrence, from the group consisting of H, alkyl, heteroalkyl, aryl, heteroaryl, and aralkyl; or R is a negative charge for instances of R bonded to a heteroatom; and m and n are integers selected, independently for each occurrence, from the range 0 to 3 inclusive.

2. The compound of claim 1, wherein X is selected from the group consisting of —C(O)—, —C(S)—, —C(NR)—, —C(R)(OR)—, —C(R)(SR)—, —P(O)(N(R)$_2$)—, —P(NR)(OR)—, and —P(NR)(N(R)$_2$)—.

3. The compound of claim 1, wherein X is —P(O)(N(R)$_2$)—.

4. The compound of claim 1, wherein Y is (C(R)$_2$)$_n$.

5. The compound of claim 1, wherein Y is (C(R)$_2$)$_n$; and n is 1.

6. The compound of claim 1, wherein Z is selected, independently for each occurrence, from the group consisting of C(R), C(N(R)$_2$), and C(NHacyl).

7. The compound of claim 1, wherein Z is C(R).

8. The compound of claim 1, wherein W is (C(R)$_2$)$_m$.

9. The compound of claim 1, wherein W is (C(R)$_2$)$_m$; and m is 2.

10. The compound of claim 1, wherein G is selected, independently for each occurrence, from the group consisting of —COOH, —C(O)NHOH, —C(O)NH$_2$, —SO$_3$H, —SO$_2$H, —S(O)$_2$NH$_2$, and —P(O)(OH)$_2$.

11. The compound of claim 1, wherein G is selected, independently for each occurrence, from the group consisting of —COOH, —C(O)NHOH, —SO$_3$H, and —P(O)(OH)$_2$.

12. The compound of claim 1, wherein G is selected, independently for each occurrence, from the group consisting of —COOH, and —C(O)NHOH.

13. The compound of claim 1, wherein G is —COOH.

14. The compound of claim 1, wherein m and n are integers selected, independently for each occurrence, from the range 1 to 2 inclusive.

15. The compound of claim 1, wherein X is selected from the group consisting of —C(O)—, —C(S)—, —C(NR)—, —C(R)(OR)—, —C(R)(SR)—, —P(O)(N(R)$_2$)—, —P(NR)(OR)—, and —P(NR)(N(R)$_2$)—; and Y is (C(R)$_2$)$_n$.

16. The compound of claim 1, wherein X is selected from the group consisting of —C(O)—, —C(S)—, —C(NR)—, —C(R)(OR)—, —C(R)(SR)—, —P(O)(N(R)$_2$)—, —P(NR)(OR)—, and —P(NR)(N(R)$_2$)—; Y is (C(R)$_2$)$_n$; and Z is selected, independently for each occurrence, from the group consisting of C(R), C(N(R)$_2$), and C(NHacyl).

17. The compound of claim 1, wherein X is selected from the group consisting of —C(O)—, —C(S)—, —C(NR)—, —C(R)(OR)—, —C(R)(SR)—, —P(O)(N(R)$_2$)—, —P(NR)(OR)—, and —P(NR)(N(R)$_2$)—; Y is (C(R)$_2$)$_n$; Z is selected, independently for each occurrence, from the group consisting of C(R), C(N(R)$_2$), and C(NHacyl); and W is (C(R)$_2$)$_m$.

18. The compound of claim 1, wherein X is selected from the group consisting of —C(O)—, —C(S)—, —C(NR)—, —C(R)(OR)—, —C(R)(SR)—, —P(O)(N(R)$_2$)—, —P(NR)(OR)—, and —P(NR)(N(R)$_2$)—; Y is (C(R)$_2$)$_n$; Z is selected, independently for each occurrence, from the group consisting of C(R), C(N(R)$_2$), and C(NHacyl); W is (C(R)$_2$)$_m$; and G is selected, independently for each occurrence, from the group consisting of —COOH, —C(O)NHOH, —C(O)NH$_2$, —SO$_3$H, —SO$_2$H, —S(O)$_2$NH$_2$, and —P(O)(OH)$_2$.

19. The compound of claim 1, wherein X is selected from the group consisting of —C(O)—, —C(S)—, —C(NR)—, —C(R)(OR)—, —C(R)(SR)—, —P(O)(N(R)$_2$)—, —P(NR)(OR)—, and —P(NR)(N(R)$_2$)—; Y is (C(R)$_2$)$_n$; Z is selected, independently for each occurrence, from the group consisting of C(R), C(N(R)$_2$), and C(NHacyl); W is (C(R)$_2$)$_m$; G is selected, independently for each occurrence, from the group consisting of —COOH, —C(O)NHOH, —C(O)NH$_2$, —SO$_3$H, —SO$_2$H, —S(O)$_2$NH$_2$, and —P(O)(OH)$_2$; and m and n are integers selected, independently for each occurrence, from the range 1 to 2 inclusive.

20. The compound of claim 1, wherein X is —P(O)(N(R)$_2$)—; and Y is (C(R)$_2$)$_n$.

21. The compound of claim 1, wherein X is —P(O)(N(R)$_2$)—; Y is (C(R)$_2$)$_n$; and Z is C(R).

22. The compound of claim 1, wherein X is —P(O)(N(R)$_2$)—; Y is (C(R)$_2$)$_n$; Z is C(R); and W is (C(R)$_2$)$_m$.

23. The compound of claim 1, wherein X is —P(O)(N(R)$_2$)—; Y is (C(R)$_2$)$_n$; Z is C(R); W is (C(R)$_2$)$_m$; and G is selected, independently for each occurrence, from the group consisting of —COOH, and —C(O)NHOH.

24. The compound of claim 1, wherein X is —P(O)(N(R)$_2$)—; Y is (C(R)$_2$)$_n$; Z is C(R); W is (C(R)$_2$)$_m$; G is selected, independently for each occurrence, from the group consisting of —COOH, and —C(O)NHOH; and m and n are integers selected, independently for each occurrence, from the range 1 to 2 inclusive.

25. A compound represented by generalized structure 2:

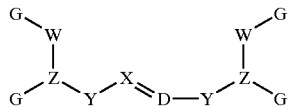

wherein

X is selected from the group consisting of —C(R)=, —C(OR)=, —C(SR)=, and —C(NR)=, Y is selected, independently for each occurrence, from the group consisting of $(C(R)_2)_n$, $(NR)_n$, $(PR)_n$, and a bond;

D is selected from the group consisting of =C(R)—, =N—, and =P—;

Z is selected, independently for each occurrence, from the group consisting of C(R), $C(N(R)_2)$, C(NHacyl), N, and P;

W is selected, independently for each occurrence, from the group consisting of $(C(R)_2)_m$, $(NR)_m$, $(PR)_m$, and a bond;

G is selected, independently for each occurrence, from the group consisting of —COOH, —C(O)NHOH, —C(O)NH$_2$, —C(S)SH, —SO$_3$H, —SO$_2$H, —SOH, —SeO$_3$H, —SeO$_2$H, —SeOH, —S(O)$_2$NH$_2$, —P(O)(OH)$_2$, and —P(OH)$_2$;

R is selected, independently for each occurrence, from the group consisting of H, alkyl, heteroalkyl, aryl, heteroaryl, and aralkyl; or R is a negative charge for instances of R bonded to a heteroatom; and m and n are integers selected, independently for each occurrence, from the range 0 to 3 inclusive.

26. The compound of claim 25, wherein X is selected from the group consisting of —C(OR)=, and —C(SR)=.

27. The compound of claim 25, wherein X is —C(SR)=.

28. The compound of claim 25, wherein Y is $(C(R)_2)_n$.

29. The compound of claim 25, wherein the instance of Y bonded to D is a bond.

30. The compound of claim 25, wherein D is =C(R)—.

31. The compound of claim 25, wherein D is =C(R)—; and the instance of Y bonded to D is a bond.

32. The compound of claim 25, wherein Z is selected, independently for each occurrence, from the group consisting of C(R), $C(N(R)_2)$, and C(NHacyl).

33. The compound of claim 25, wherein Z is C(R).

34. The compound of claim 25, wherein W is $(C(R)_2)_m$.

35. The compound of claim 25, wherein W is $(C(R)_2)_m$; and m is 2.

36. The compound of claim 25, wherein G is selected, independently for each occurrence, from the group consisting of —COOH, —C(O)NHOH, —C(O)NH$_2$, —SO$_3$H, —SO$_2$H, —S(O)$_2$NH$_2$, and —P(O)(OH)$_2$.

37. The compound of claim 25, wherein G is selected, independently for each occurrence, from the group consisting of —COOH, —C(O)NHOH, —SO$_3$H, and —P(O)(OH)$_2$.

38. The compound of claim 25, wherein G is selected, independently for each occurrence, from the group consisting of —COOH, and —C(O)NHOH.

39. The compound of claim 25, wherein G is —COOH.

40. The compound of claim 25, wherein m and n are independently for each occurrence 0, 1, or 2.

41. The compound of claim 25, wherein X is selected from the group consisting of —C(OR)=, and —C(SR)=, and Y is $(C(R)_2)_n$.

42. The compound of claim 25, wherein X is selected from the group consisting of —C(OR)=, and —C(SR)=; and D is =C(R)—.

43. The compound of claim 25, wherein X is selected from the group consisting of —C(OR)=, and —C(SR)=; D is =C(R)—; and the instance of Y bonded to D is a bond.

44. The compound of claim 25, wherein X is selected from the group consisting of —C(OR)=, and —C(SR)=; Y is $(C(R)_2)_n$; and Z is selected, independently for each occurrence, from the group consisting of C(R), $C(N(R)_2)$, and C(NHacyl).

45. The compound of claim 25, wherein X is selected from the group consisting of —C(OR)=, and —C(SR)=; Y is $(C(R)_2)_n$; Z is selected, independently for each occurrence, from the group consisting of C(R), $C(N(R)_2)$, and C(NHacyl); and W is $(C(R)_2)_m$.

46. The compound of claim 25, wherein X is selected from the group consisting of —C(OR)=, and —C(SR)=; Y is $(C(R)_2)_n$; Z is selected, independently for each occurrence, from the group consisting of C(R), $C(N(R)_2)$, and C(NHacyl); W is $(C(R)_2)_m$; and G is selected, independently for each occurrence, from the group consisting of —COOH, —C(O)NHOH, —C(O)NH$_2$, —SO$_3$H, —SO$_2$H, —S(O)$_2$NH$_2$, and —P(O)(OH)$_2$.

47. The compound of claim 25, wherein X is selected from the group consisting of —C(OR)=, and —C(SR)=; Y is $(C(R)_2)_n$; Z is selected, independently for each occurrence, from the group consisting of C(R), $C(N(R)_2)$, and C(NHacyl); W is $(C(R)_2)_m$; G is selected, independently for each occurrence, from the group consisting of —COOH, —C(O)NHOH, —C(O)NH$_2$, —SO$_3$H, —SO$_2$H, —S(O)$_2$NH$_2$, and —P(O)(OH)$_2$; and m and n are independently for each occurrence 0, 1, or 2.

48. The compound of claim 25, wherein X is —C(SR)=; and Y is $(C(R)_2)_n$.

49. The compound of claim 25, wherein X is —C(SR)=; and D is =C(R).

50. The compound of claim 25, wherein X is —C(SR)=; D is =C(R)—; and the instance of Y bonded to D is a bond.

51. The compound of claim 25, wherein X is —C(SR)=; Y is $(C(R)_2)_n$; and Z is C(R).

52. The compound of claim 25, wherein X is —C(SR)=; Y is $(C(R)_2)_n$; Z is C(R); and W is $(C(R)_2)_m$.

53. The compound of claim 25, wherein X is —C(SR)=; Y is $(C(R)_2)_n$; Z is C(R); W is $(C(R)_2)_m$; and G is selected, independently for each occurrence, from the group consisting of —COOH, and —C(O)NHOH.

54. The compound of claim 25, wherein X is —C(SR)=; Y is $(C(R)_2)_n$; Z is C(R); W is $(C(R)_2)_m$; G is selected, independently for each occurrence, from the group consisting of —COOH, and —C(O)NHOH; and m and n are independently for each occurrence 0, 1, or 2.

55. The compound of any one of claims 1–54, wherein the compound is a ligand for a metabotropic glutamate receptor.

56. The compound of any one of claims 1–54, wherein the compound is an agonist of a metabotropic glutamate receptor.

57. The compound of any one of claims 1–54, wherein the compound is a antagonist of a metabotropic glutamate receptor.

58. The compound of any one of claims 1–54, wherein the compound is a ligand for a single subtype of metabotropic glutamate receptor.

59. The compound of any one of claims 1–54, wherein the compound is an agonist of a single subtype of metabotropic glutamate receptors.

60. The compound of any one of claims 1–54, wherein the compound is an antagonist of a single subtype of metabotropic glutamate receptors.

61. The compound of any one of claims 1–54, wherein the compound is an inhibitor of NAALADase.

62. A pharmaceutical composition comprising a compound of any one of claims 1–54.

63. A method of inhibiting NAALADase in a subject in need thereof, comprising the step of administering to the subject a composition comprising a compound of claim 61.

64. A method of agonising a metabotropic glutamate receptor in a mammal, comprising the step of administering to said mammal an effective amount of a compound of claim 56.

65. A method of antagonising a metabotropic glutamate receptor in a mammal, comprising the step of administering to said mammal an effective amount of a compound of claim 57.

66. A method of agonising a single subtype of metabotropic glutamate receptor in a mammal, comprising the step of administering to said mammal an effective amount of a compound of claim 59.

67. A method of antagonising a single subtype of metabotropic glutamate receptor in a mammal, comprising the step of administering to said mammal an effective amount of a compound of claim 60.

* * * * *